(12) United States Patent
Anzai et al.

(10) Patent No.: US 10,758,657 B2
(45) Date of Patent: *Sep. 1, 2020

(54) ARTIFICIAL LUNG AND METHOD FOR MANUFACTURING ARTIFICIAL LUNG

(71) Applicant: TERUMO KABUSHIKI KAISHA, Shibuya-ku, Tokyo (JP)

(72) Inventors: Takao Anzai, Kanagawa (JP); Eisuke Sasaki, Elkton, MD (US); Norikazu Ishida, Kanagawa (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 483 days.

This patent is subject to a terminal disclaimer.

(21) Appl. No.: 15/699,284

(22) Filed: Sep. 8, 2017

(65) Prior Publication Data
US 2018/0036468 A1 Feb. 8, 2018

Related U.S. Application Data

(63) Continuation of application No. PCT/JP2016/057027, filed on Mar. 7, 2016.

(30) Foreign Application Priority Data

Mar. 10, 2015 (JP) .................................. 2015-047600
Jul. 29, 2015 (JP) .................................. 2015-150084

(51) Int. Cl.
*A61M 1/16* (2006.01)
*B01D 67/00* (2006.01)
(Continued)

(52) U.S. Cl.
CPC ........ *A61M 1/1698* (2013.01); *A61M 1/1621* (2014.02); *B01D 67/0088* (2013.01);
(Continued)

(58) Field of Classification Search
CPC .............. A61M 1/1698; A61M 1/1678; A61M 1/1621; A61M 1/1625; A61M 1/1627;
(Continued)

(56) References Cited

U.S. PATENT DOCUMENTS 6,495,101 B1 * 12/2002 Yokoyama ........... B01D 63/021
128/DIG. 23
2014/0231333 A1 8/2014 Kelada

FOREIGN PATENT DOCUMENTS

EP 0 041 692 A1 12/1981
JP 57-3652 A 1/1982
(Continued)

OTHER PUBLICATIONS

International Search Report (PCT/ISA/210) dated May 24, 2016, by the Japanese Patent Office as the International Searching Authority for International Application No. PCT/JP2016/057027.
(Continued)

*Primary Examiner* — Philip R Wiest
(74) *Attorney, Agent, or Firm* — Buchanan Ingersoll & Rooney PC

(57) ABSTRACT

An artificial lung is provided that includes a plurality of porous hollow fiber membranes for gas exchange comprising a hydrophobic polymer material, wherein the hollow fiber membranes have inner surfaces forming lumens and outer surfaces, and wherein at least one of the inner surfaces or the outer surfaces is coated with a polymer-containing solution that has a surface tension of 40 to 55 dyn/cm and that contains a solvent and a polymer having a structural unit represented by Formula (I):
(Continued)

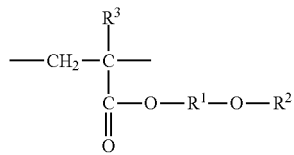

$$\begin{array}{c} \quad\quad R^3 \\ \quad\quad | \\ -CH_2-C- \\ \quad\quad | \\ \quad\quad C-O-R^1-O-R^2 \\ \quad\quad \| \\ \quad\quad O \end{array} \quad (I)$$

wherein in Formula (I), $R^3$ represents a hydrogen atom or a methyl group, $R^1$ represents an alkylene group having 1 to 4 carbon atoms, and $R^2$ represents an alkyl group having 1 to 4 carbon atoms.

21 Claims, 7 Drawing Sheets

(51) Int. Cl.
*B01D 69/02* (2006.01)
*B01D 63/02* (2006.01)

(52) U.S. Cl.
CPC ..... *B01D 69/02* (2013.01); *A61M 2205/7536* (2013.01); *A61M 2207/00* (2013.01); *B01D 63/02* (2013.01); *B01D 2325/04* (2013.01)

(58) Field of Classification Search
CPC ...... A61M 2205/7536; A61M 2207/00; B01D 67/0088; B01D 69/02; B01D 63/02; B01D 2325/04
See application file for complete search history.

(56) References Cited

FOREIGN PATENT DOCUMENTS

| | | |
|---|---|---|
| JP | 11-114056 A | 4/1999 |
| JP | 3908839 B2 | 1/2007 |
| JP | 4317183 B2 | 5/2009 |

OTHER PUBLICATIONS

Written Opinion of the International Searching Authority (Form PCT/ISA/237) dated May 24, 2016, in the corresponding International Application No. PCT/JP2016/057027. (4 pages).

\* cited by examiner

ARTIFICIAL LUNG AND METHOD FOR MANUFACTURING ARTIFICIAL LUNG

CROSS-REFERENCES TO RELATED APPLICATIONS

This application is a continuation of International Application No. PCT/JP2016/057027 filed on Mar. 7, 2016, and claims priority to Japanese Application No. 2015-047600 filed on Mar. 10, 2015 and Japanese Application No. 2015-150084 filed on Jul. 29, 2015, the entire content of all three of which is incorporated herein by reference.

TECHNICAL FIELD

The present disclosure generally relates to an artificial lung and a method for manufacturing an artificial lung. The present disclosure generally relates to a hollow fiber membrane type artificial lung for removing carbon dioxide in the blood and adding oxygen to the blood in extracorporeal blood circulation, for example, a hollow fiber membrane artificial lung of an outside blood flow type, and a method for manufacturing the same.

BACKGROUND DISCUSSION

A hollow fiber membrane type artificial lung using porous membranes generally can be used as an extracorporeal circulator or an artificial heart-lung apparatus for assisting circulation in open heart surgery for a heart disease. The hollow fiber membranes can be used for membrane type artificial lungs. Gas exchange in blood is performed through these hollow fiber membranes. As a system of blood flow to the artificial lung, there are an inside flow system in which the blood flows inside of the hollow fiber membranes and gas flows outside of the hollow fiber membranes, and an outside flow system in which, by comparison, the blood flows outside of the hollow fiber membranes and gas flows inside of the hollow fiber membranes.

In hollow fiber membrane type artificial lungs, inner surfaces or outer surfaces of the hollow fiber membranes are in contact with the blood. Therefore, there is a concern that the inner surfaces or the outer surfaces of the hollow fiber membranes in contact with the blood may affect adhesion (attachment) or activation of the platelet system. For example, an outside flow type artificial lung in which the outer surfaces of the hollow fiber membranes are in contact with the blood can generate a blood flow which can cause adhesion (attachment) or activation of the platelet system.

Considering such problems, and in view of the suppression and prevention effects of alkoxyalkyl (meth)acrylate on adhesion or activation of the platelet system, alkoxyalkyl (meth)acrylate can be used for coating the hollow fiber membranes of an outside flow type artificial lung. For example, U.S. Pat. No. 6,495,101 B1 (corresponding to JP-A-11-114056 and EP 0 908 191 A1) discloses that outside surfaces or outer surface layers of the hollow fiber membranes are coated with a coating solution obtained by dissolving a polymer containing alkoxyalkyl (meth)acrylate as a main component in a mixed solvent of water, methanol and ethanol, and then dried.

SUMMARY

In a hollow fiber membrane artificial lung of an outside blood flow type (e.g., manufactured by the method disclosed in U.S. Pat. No. 6,495,101 B1), adhesion or activation of the platelets can be suppressed and leakage of blood plasma components can be reduced.

Meanwhile, reducing the amount of blood taken out of the body (the amount of blood outflow) reduces the burden on a patient. It can be desirable, for example, to reduce the size of the artificial lung by making a wall thickness of the hollow fiber membranes thin.

However, thinning the hollow fiber membrane and the leakage of blood plasma components are in a trade-off relationship. Regardless of the flow systems, it can be desirable that the leakage of blood plasma components after circulation (blood plasma leakage) is further suppressed even in the thin-walled hollow fiber membranes.

Accordingly, aspects of the disclosure have been made in view of the above circumstances. According to an exemplary aspect, an artificial lung is provided that can suppress the leakage of blood plasma components (blood plasma leakage) even in thin-walled hollow fiber membranes.

According to an exemplary aspect of the present disclosure, an artificial lung is provided that can suppress elution of a coating (for example, a polymer) into blood.

As a result of intensive research to ameliorate or overcome the above problems, the inventors of the present invention have found, for example, that the above problems can be ameliorated or overcome by adjusting a surface tension of a coating solution containing an alkoxyalkyl (meth)acrylate polymer to a specific range. Aspects of the present disclosure have been completed based on the above findings.

According to one aspect, provided is an artificial lung including a plurality of porous hollow fiber membranes for gas exchange made of a hydrophobic polymer material, in which the hollow fiber membranes have inner surfaces forming lumens and outer surfaces.

Any one of the inner surface or the outer surface is coated with a polymer-containing solution that has a surface tension of 40 to 55 dyn/cm and that contains a solvent and a polymer having a structural unit derived from alkoxyalkyl (meth) acrylate represented by Formula (I):

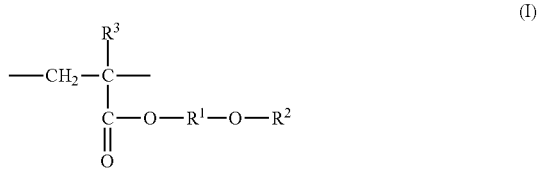

According to one aspect, provided is a method for manufacturing an artificial lung that has a plurality of porous hollow fiber membranes for gas exchange made of a hydrophobic polymer material, in which the hollow fiber membranes have inner surfaces forming lumens and outer surfaces, the method including coating the inner surfaces forming the lumens of the hollow fiber membranes or the outer surfaces with a polymer-containing solution that has a surface tension of 40 to 55 dyn/cm and that contains a solvent and a polymer having a structural unit derived from alkoxyalkyl (meth)acrylate represented by Formula (I).

According to one aspect, provided is an artificial lung including a plurality of porous hollow fiber membranes for gas exchange made of a hydrophobic polymer material, in which the hollow fiber membranes have inner surfaces forming lumens and outer surfaces, a wall thickness between the inner surfaces and the outer surfaces is 20 µm or more and less than 50 μm, one of the inner surfaces or the outer surfaces is coated with a coating that contains a polymer having a structural unit derived from alkoxyalkyl (meth) acrylate represented by Formula (I), and a blood plasma leakage resistance performance of the artifical lung is 15 mmHg or less.

BRIEF DESCRIPTION OF THE DRAWINGS

FIG. 1 depicts a hollow fiber membrane artificial lung of an outside blood flow type 1, a housing 2, a hollow fiber membrane 3, partition walls 4 and 5, a blood inlet port 6, a blood outlet port 7, and a blood chamber 12.

FIG. 2 depicts an outer surface layer 3a, an internal layer 3b, an inner surface layer 3c, and a polymer 18.

FIG. 3 depicts a blood chamber 17, a hollow fiber membrane artificial lung of an outside blood flow type 20, a tubular hollow fiber membrane bundle 22, a housing 23, a gas inlet port 24, partition walls 25 and 26, a gas outlet port 27, a blood inlet port 28, a blood outlet port 29, an inner tubular member 31, and a blood circulation opening 32.

FIG. 4 depicts a hollow fiber membrane 3, a tubular hollow fiber membrane bundle 22, and a blood circulation opening 32.

FIG. 5 depicts an inner tubular member 31 and a blood circulation opening 32.

FIG. 6 depicts an inner tubular member 31 and a blood circulation opening 32.

FIG. 7 depicts an inner tubular member 31 and a blood circulation opening 32.

DETAILED DESCRIPTION

Figure 1:
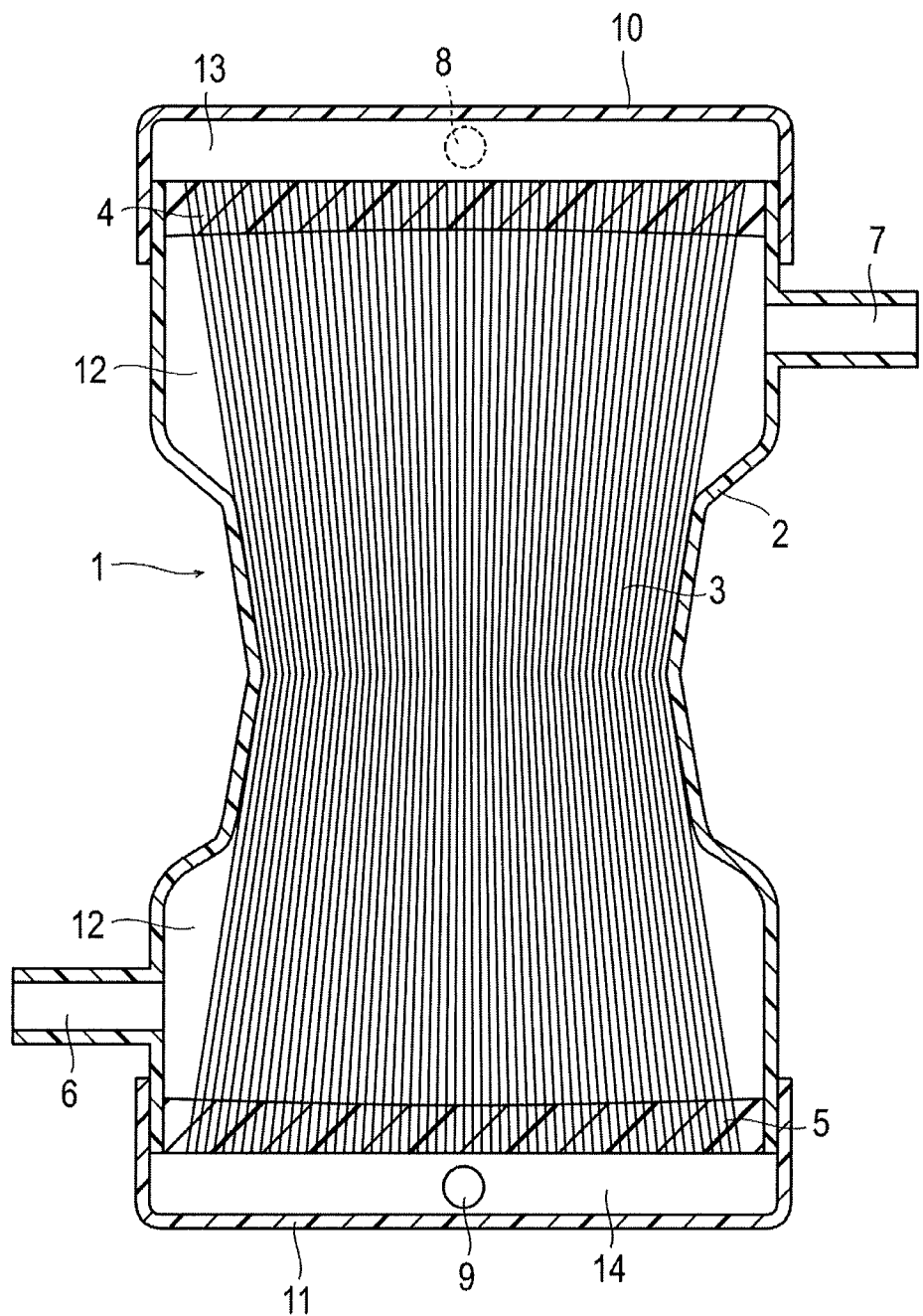
FIG. 1 is a cross-sectional view showing one embodiment of a hollow fiber membrane artificial lung of an outside blood flow type, according to one aspect.

Set forth below with reference to the accompanying drawings is a detailed description of exemplary embodiments of an artificial lung and a method of manufacturing an artificial lung.

Disclosed is an artificial lung that has a plurality of porous hollow fiber membranes for gas exchange made of a hydrophobic polymer material, in which the hollow fiber membranes have inner surfaces forming lumens and outer surfaces.

One of the inner surfaces or the outer surfaces is coated with a polymer-containing solution that has a surface tension of 40 to 55 dyn/cm and that contains a solvent and a polymer (hereinafter may also be referred to as "polymer according to one aspect of the present disclosure" or "alkoxyalkyl (meth)acrylate polymer") having a structural unit represented by Formula (I):

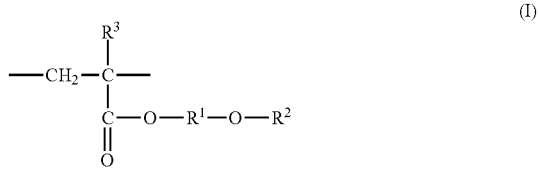

in which $R^3$ represents a hydrogen atom or a methyl group, $R^1$ represents an alkylene group having 1 to 4 carbon atoms, and $R^2$ represents an alkyl group having 1 to 4 carbon atoms. The structural unit represented by Formula (I) can be a repeating unit derived from alkoxyalkyl (meth)acrylate. For example, by using the artificial lung having the above configuration, the leakage of blood plasma components (blood plasma leakage) can be suppressed or prevented, for example, even in thin-walled hollow fiber membranes.

In addition, disclosed is a method for manufacturing an artificial lung that has a plurality of porous hollow fiber membranes for gas exchange made of a hydrophobic polymer material, in which the hollow fiber membranes have inner surfaces forming lumens and outer surfaces, the method including: coating the inner surfaces forming the lumens of the hollow fiber membranes or the outer surfaces with a polymer-containing solution that has a surface tension of 40 to 55 dyn/cm and that contains a solvent and a polymer having a structural unit derived from alkoxyalkyl (meth) acrylate represented by Formula (I). For example, by using the method, it is possible to manufacture an artificial lung by which the leakage of blood plasma components (blood plasma leakage) can be suppressed or prevented even in thin-walled hollow fiber membranes.

Disclosed is an artificial lung in which a coating formed by coating the outer surfaces or inner surfaces of the hollow fiber membranes with the polymer-containing solution having a specific surface tension, is provided on the outer surfaces or the inner surfaces of the hollow fiber membranes. The artificial lung using the hollow fiber membranes having the coating can suppress or prevent the leakage of blood plasma components (blood plasma leakage) after circulation, for example, in thin-walled hollow fiber membranes. An exemplary mechanism exhibiting the above effects by the configuration of an exemplary aspect is disclosed as follows. The present invention is not limited to the following mechanism.

An artificial lung is produced by allowing a polymer-containing solution in which poly methoxyethyl acrylate is dissolved in a mixed solvent of water, methanol, and ethanol (6:1:3) to flow to outer surfaces of hollow fiber membranes (blood flowing side) having a wall thickness of 50 μm. Thereafter, the entire blood contact portion of the artificial lung is coated with a synthetic polymer. In the artificial lung produced by such a method, the leakage of blood plasma components is certainly reduced. The inventors of the present invention made the wall thickness of the hollow fiber membranes of the artificial lung thinner so as to reduce the size of the artificial lung (for example, to reduce the burden on a patient). As a result, the leakage of the blood plasma components (blood plasma leakage) from the artificial lung (for example, the hollow fiber membranes) during or after the circulation was observed more frequently as the wall thickness became thinner.

Intensive research was conducted to determine the reason for the blood plasma leakage (and therefore, a deterioration in gas exchange capacity) in the thin-walled hollow fiber membranes. Generally, when coating the entire blood contact portion of porous hollow fiber membranes for gas exchange with the polymer-containing solution, the polymer-containing solution penetrates into fine holes of the hollow fiber membranes, and the coating of the polymer is formed on an inner wall of the fine holes of the blood flowing side. If the blood circulates in such an artificial lung, the blood plasma components infiltrate into the fine holes along the coating of the polymer. In the hollow fiber membranes having a thick wall thickness (i.e., membrane thickness), there is a large difference between an outer diameter and an inner diameter. In such hollow fiber membranes having a thick wall thickness, because the coating of the polymer is not entirely formed on the entire inner wall of the fine holes (that is, the coating of the polymer does not extend to the hollow fiber membrane surface on a side where the coating is not formed), the leakage of the blood plasma components (blood plasma leakage) into a lumen along the coating of the polymer occurs less or does not occur. In contrast, in the thin-walled hollow fiber membranes (where there is a small difference between the outer diameter and the inner diameter), because the coating of the polymer is completely formed on the entire inner wall of the fine holes easily (that is, the coating of the polymer extends to the hollow fiber membrane surface on a side where the coating is not formed), the leakage of the blood plasma components into a lumen along the fine holes is likely to occur (see, e.g., the following Comparative Example 1). Therefore, the problem of deterioration in the gas exchange capacity is likely to occur.

Considering the above circumstances, it may be desirable, for example, to suppress the penetration of the polymer into the fine holes so as to reduce the blood plasma leakage in the thin-walled hollow fiber membranes. I The present inventors conducted intensive research, for example, for a method for suppressing the penetration of the polymer into the fine holes. As a result, by setting the surface tension of the polymer-containing solution (application solution) to a high value of 40 to 55 dyn/cm when forming the coating of the polymer on the outer surfaces of the hollow fiber membranes (in the case of the hollow fiber membrane artificial lung of an outside blood flow type) or the inner surfaces (in the case of the hollow fiber membrane artificial lung of an inside blood flow type), it has been found that a risk of the penetration of the polymer-containing solution (application solution) into internal layers of the hollow fiber membranes can be suppressed. For example, even in a case where porous membranes for gas exchange are thin and in a case where a coating solution is applied in a large amount, the inner surface layers of the porous hollow fiber membranes for gas exchange (in the case of the hollow fiber membrane artificial lung of an outside blood flow type) or the outer surface layers (in the case of the hollow fiber membrane artificial lung of an inside blood flow type) maintain the hydrophobic state of the forming material and have a high level of the leakage prevention effect of blood plasma. Therefore, an exemplary artificial lung can effectively suppress or prevent the leakage of the blood (for example, blood plasma components) to a side opposite to the blood flowing side, for example, even in thin-walled hollow fiber membranes.

The above exemplary effects are significantly achieved, for example, in a case where the wall thickness of the hollow fiber membranes is less than 50 μm. Therefore, aspects of the present disclosure provide an artificial lung that has a plurality of porous hollow fiber membranes for gas exchange made of a hydrophobic polymer material, in which the hollow fiber membranes have inner surfaces forming lumens and outer surfaces, a wall thickness between the inner surface and the outer surface is 20 μm or more and less than 50 μm, any one of the inner surface or the outer surface is coated with a coating that contains a polymer having a structural unit derived from alkoxyalkyl (meth)acrylate represented by Formula (I), and blood plasma leakage performance is 15 mmHg or less.

Furthermore, generally, in a case where the surface tension of the polymer-containing solution (application solution) is as high as that of aspects of the present disclosure, uniformly dissolving a polymer in the polymer-containing solution (application solution) is generally difficult. Polymers of a certain degree of molecular weight distribution are dissolved in the polymer-containing solution, but it is found that a polymer having a low molecular weight is likely to be eluted into blood. Therefore, by using a polymer having a particularly high molecular weight in a polymer-containing application solution, the content of the polymer having a low molecular weight in the coating is reduced, and thus the elution of the coating (for example, the polymer) into the blood can be suppressed, which can be desirable.

In addition, an exemplary polymer has excellent antithrombotic activity and biocompatibility (the suppression and prevention effects of adhesion and attachment of the platelets and the suppression and prevention effects of activation of the platelets), for example, the suppression and prevention effects of adhesion and attachment of the platelets. Therefore, an exemplary artificial lung has excellent antithrombotic activity and biocompatibility (the suppression and prevention effects of adhesion and attachment of the platelets and the suppression and prevention effects of activation of the platelets), for example, the suppression and prevention effects of adhesion and attachment of the platelets.

Hereinafter, exemplary embodiments will be described. The present invention is not limited only to the following embodiments. Specifically, hereinafter, the hollow fiber membrane artificial lung of an outside blood flow type will be described as an exemplary embodiment, but the artificial lung may be the hollow fiber membrane artificial lung of an inside blood flow type. The following embodiments can be appropriately adopted for use in either a hollow fiber membrane artificial lung of an outside blood flow type or a hollow fiber membrane artificial lung of an inside blood flow type. Furthermore, the dimensions employed in the drawings may be exaggerated for convenience of description and may differ from the actual dimensions in some cases.

In the present specification, "X to Y" indicating a range includeing X and Y, and means "X or more and Y or less". In addition, unless otherwise specified, operation and measurements of physical properties or the like are measured under conditions of room temperature (20° C. to 25° C.) and at a relative humidity of 40% to 50%.

<Artificial Lung>

Hereinafter, an exemplary artificial lung will be explained while referring to the drawings.

Figure 2:
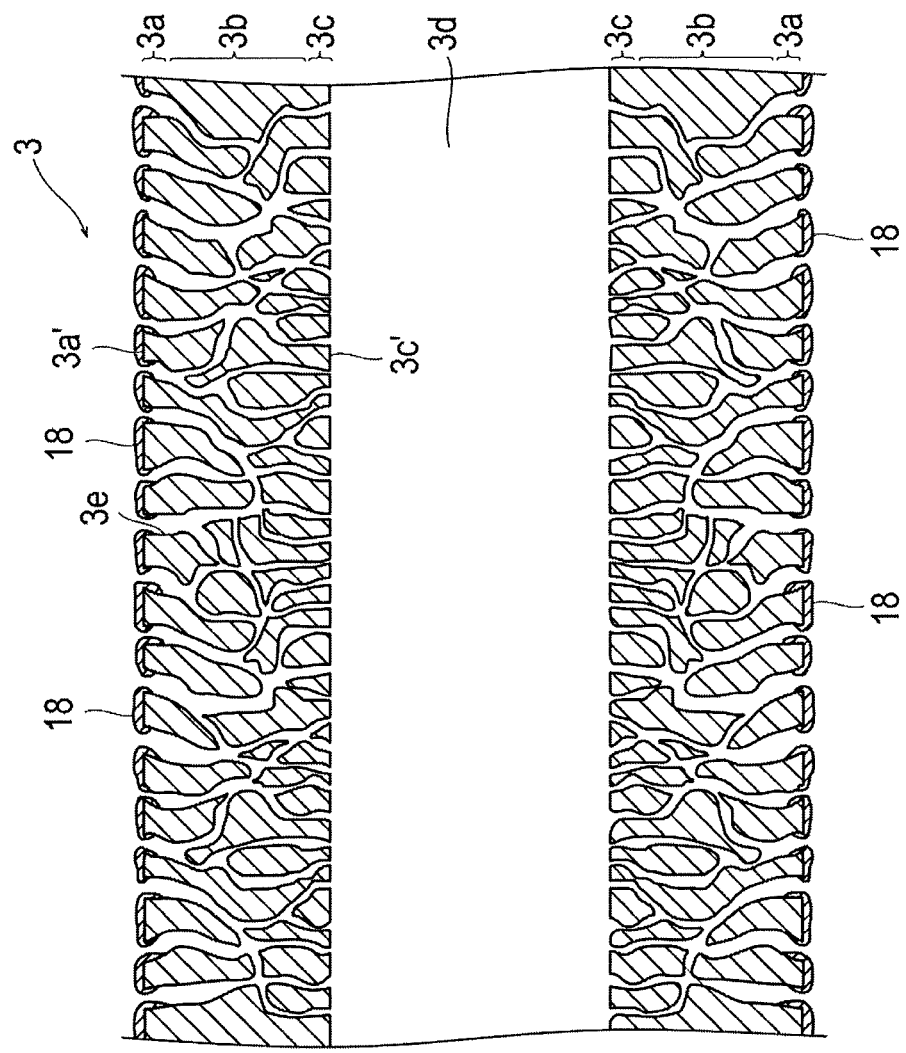
FIG. 2 is an enlarged cross-sectional view of the hollow fiber membranes used for the hollow fiber membrane artificial lung of an outside blood flow type, according to one aspect.
Figure 3:
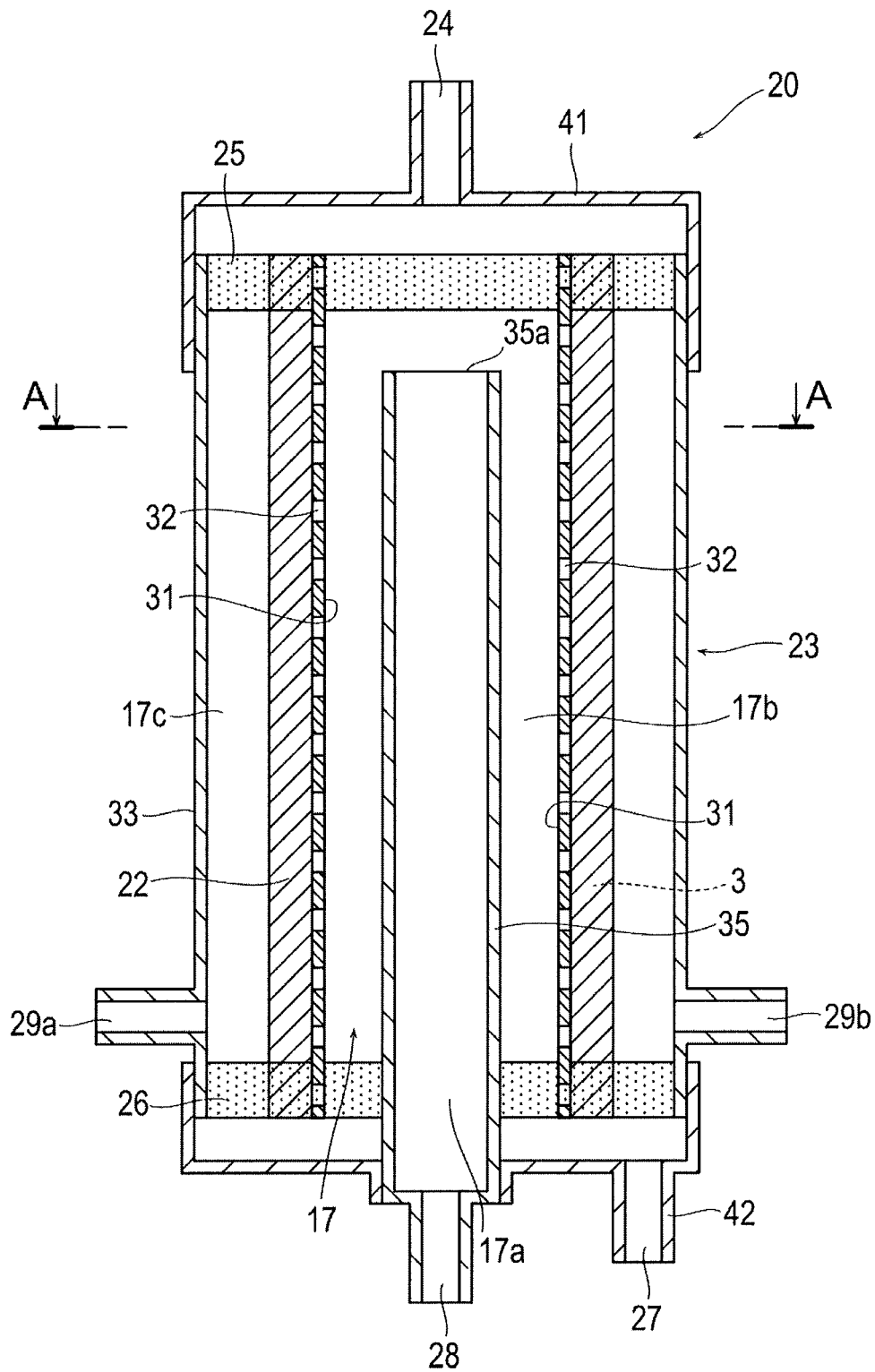
FIG. 3 is a cross-sectional view showing another embodiment of a hollow fiber membrane artificial lung of an outside blood flow type, according to one aspect.

FIG. 1 is a cross-sectional view of one embodiment of a hollow fiber membrane artificial lung of an outside blood flow type. FIG. 2 is an enlarged cross-sectional view of the porous hollow fiber membranes for gas exchange used for the hollow fiber membrane artificial lung of an outside blood flow type. FIG. 3 is a cross-sectional view of another embodiment of an artificial lung.

In FIG. 1, an artificial lung 1 is an artificial lung type in which a large number of porous hollow fiber membranes 3 for gas exchange are accommodated in a housing 2. The blood flows into the outer side of the hollow fiber membranes 3, and an oxygen-containing gas flows to the inside of the hollow fiber membranes 3. In FIG. 2, a polymer (alkoxyalkyl (meth)acrylate polymer) 18 coats the outside surface 3a' (and optionally the outer surface layer 3a) of the hollow fiber membrane 3 which serves as the blood contact portion. A coating of the polymer (alkoxyalkyl (meth)acrylate polymer) 18 is selectively formed on the outer surface 3a' (and optionally the outer surface layer 3a) of the hollow fiber membranes 3. FIG. 2 shows an aspect where the coating of the polymer 18 is formed on the outer surface 3a' of the hollow fiber membrane used in the hollow fiber membrane artificial lung of an outside blood flow type. In the hollow fiber membrane of such an aspect, the outer surface 3a' side is in contact with the blood, and the oxygen-containing gas flows and contacts an inner surface 3c'. In another embodiment, the artificial lung is a hollow fiber membrane artificial lung of an inside blood flow type, as described above. Accordingly, the hollow fiber membrane may have a reversed configuration with respect to the above aspect. That is, the coating of the polymer 18 can be formed on the inner surface 3c' in the case of an artificial lung of an inside blood flow type.

In an exemplary embodiment, a polymer coats an outside surface of a hollow fiber membrane. For example, the coating of the polymer is formed on the outer surface of the hollow fiber membrane (a surface on the side where the blood flows) or on the outer surface and the outer surface layer. In an exemplary embodiment, a polymer coats an outer surface of a hollow fiber membrane. For example, the coating of the polymer is formed on the outer surface of the hollow fiber membrane (a surface on the side where the blood flows). In an exemplary embodiment, a polymer coats an outer surface layer of a hollow fiber membrane. For example, the polymer penetrates into a part of the outer surface layer of the hollow fiber membrane (for example, in the vicinity of the outer surfaces of the fine holes) to form the coating. In such a case, for example, no substantial polymer exists on the inside surface (inner surface) of the hollow fiber membrane (a surface on the side where the oxygen-containing gas flows) as described below in detail. That is, for example, the coating of the polymer according to one aspect of the present disclosure is selectively formed on the blood contact portion of the hollow fiber membrane (outer surface). Note that the coating of the polymer according to one aspect of the present disclosure may be formed on at least a part of the blood contact portion of the hollow fiber membrane (outer surface), but it is exemplary that the coat is formed on the entire blood contact portion of the hollow fiber membrane (outer surface) from the viewpoint of the antithrombotic activity and biocompatibility (for example, the suppression and prevention effects of adhesion and attachment of the platelets and the suppression and prevention effects of activation of the platelets). That is, the polymer can coat the entire blood contact portion of the artificial lung (outer surface).

In the embodiment according to FIG. 2, the polymer may exist on an internal layer 3b or an inner surface layer 3c of the hollow fiber membrane 3, but it is exemplary that no substantial polymer exists on the internal layer 3b or the inner surface layer 3c of the hollow fiber membrane 3. In the present specification, "no substantial polymer according to one aspect of the present disclosure exists on the internal layer 3b or the inner surface layer 3c of the hollow fiber membrane 3" means that the penetration of the polymer according to one aspect of the present disclosure was not observed in the vicinity of the inside surface of the hollow fiber membrane (a surface on the side where the oxygen-containing gas flows).

A hollow fiber membrane type artificial lung 1 includes a housing 2 having a blood inlet port 6 and a blood outlet port 7, a hollow fiber membrane bundle having a large number of porous hollow fiber membranes 3 for gas exchange accommodated in the housing 2. A pair of partition walls 4 and 5 liquid-tightly support both end portions of the hollow fiber membrane bundle within the housing 2. A blood chamber 12 is formed between the inside surface of the housing 2 and the partition walls 4 and 5, and the outside surfaces of the hollow fiber membranes 3. A gas chamber is formed inside the hollow fiber membranes 3. A gas inlet port 8 and a gas outlet port 9 communicate with the gas chamber.

The hollow fiber membrane type artificial lung 1 includes the tubular housing 2, an aggregate of the hollow fiber membranes 3 for gas exchange accommodated in the tubular housing 2, and the partition walls 4 and 5 liquid-tightly retaining both end portions of the hollow fiber membranes 3 within the housing 2. The tubular housing 2 is partitioned into the blood chamber 12 that is a first fluid chamber and the gas chamber that is a second fluid chamber. The blood inlet port 6 and the blood outlet port 7 communicating with the blood chamber 12 are provided in the tubular housing 2.

A cap-like gas inlet side header 10 having the gas inlet port 8 that is a second fluid inlet port communicating with the gas chamber that is the inner spaces of the hollow fiber membranes 3, is attached above the partition walls 4 that are the end portion of the tubular housing 2. A gas inlet chamber 13 is formed of the outside surface of the partition walls 4 and the inside surface of the gas inlet side header 10. The gas inlet chamber 13 communicates with the gas chamber that is formed of the inner spaces of the hollow fiber membranes 3.

A cap-like gas outlet side header 11 having a gas outlet port 9 that is a second fluid outlet port communicating with the inner spaces of the hollow fiber membranes 3, is attached below the partition walls 5. A gas outlet chamber 14 is formed of the outside surface of the partition walls 5 and the inside surface of the gas outlet side header 11.

The hollow fiber membranes 3 are porous membranes made of a hydrophobic polymer material. Membranes suitable for use as hollow fiber membranes in an artificial lung can be used and are not particularly limited. The hollow fiber membranes (for example, the inside surfaces of the hollow fiber membranes) are made of a hydrophobic polymer material, and thus the leakage of blood plasma components can be suppressed.

An inner diameter of the hollow fiber membrane is not particularly limited, but can be 50 to 300 μm, for example, 80 to 200 μm. An outer diameter of the hollow fiber membrane is not particularly limited, but can be 100 to 400 μm, for example, 130 to 200 μm. The wall thickness of the hollow fiber membrane (membrane thickness) is not particularly limited, but can be 20 μm or more and less than 50 for example, 25 μm or more and less than 50 μm, for example, 25 to 45 μm, for example, 25 to 40 μm, for example, 25 to 35 μm, for example, 25 to 30 μm. In the present specification, "the wall thickness of the hollow fiber membrane" means a wall thickness between the inner surface and the outer surface of the hollow fiber membrane, and is calculated by using the expression: [(outer diameter of hollow fiber membrane)−(inner diameter of hollow fiber membrane)]/2. The wall thickness between the inner surface and the outer surface of the hollow fiber membrane can be 20 µm or more and less than 50 µm, for example, 25 µm or more and less than 50 µm, for example, 25 to 45 µm, for example, 25 to 40 µm, for example, 25 to 35 µm, for example, 25 to 30 µm. For example, by setting a lower limit of the wall thickness of the hollow fiber membrane as above, it is possible to secure the sufficient strength of the hollow fiber membranes. Furthermore, for example, it is satisfactory in terms of labor and cost in manufacturing, and is also exemplary from the viewpoint of mass production. Furthermore, porosity of the hollow fiber membrane is not particularly limited and can be 5 to 90% by volume, for example, 10% to 80% by volume, for example, 30% to 60% by volume. A fine hole diameter of the hollow fiber membrane is not particularly limited and can be 0.01 to 5 µm, for example, 0.05 to 1 µm. In addition, as a material used for the porous membranes, the same material as the hollow fiber membranes used for an artificial lung can be used. For example, there are a polyolefin resin such as polypropylene and polyethylene, a hydrophobic polymer material such as polysulfone, polyacrylonitrile, polytetrafluoroethylene, and cellulose acetate, and the like. Among these, a polyolefin resin can be used, and polypropylene is exemplary. The method for manufacturing hollow fiber membranes is not particularly limited, and any suitable method for manufacturing hollow fiber membranes can be applied and modified, if appropriate. For example, it is exemplary that micro fine holes are formed on the walls of the hollow fiber membranes through a stretching method or a solid-liquid phase separation method.

As a material constituting the tubular housing 2, the same material as a material used for a housing of an artificial lung can be used. For example, there is a hydrophobic synthetic resin such as polycarbonate, acrylic-styrene copolymer, and acrylic-butylene-styrene copolymer. A shape of the housing 2 is not particularly limited, but can be cylindrical and transparent, for example. The inside thereof can be easily confirmed by forming the housing to be transparent.

An amount of the hollow fiber membranes accommodated in the housing 2 is not particularly limited. For example, about 5,000 to 100,000 porous hollow fiber membranes 3 are accommodated in parallel in the housing 2 in an axial direction thereof. Furthermore, in a state where both the ends of the hollow fiber membranes 3 are respectively open towards both the ends of the housing 2, the hollow fiber membranes 3 are fixed in a liquid-tight state by the partition walls 4 and 5. The partition walls 4 and 5 are formed by a potting agent such as polyurethane and silicone rubber. A portion interposed between the above partition walls 4 and 5 in the housing 2 is divided into the gas chamber inside the hollow fiber membranes 3 and the blood chamber 12 outside the hollow fiber membranes 3.

In the present embodiment, the gas inlet side header 10 having the gas inlet port 8 and the gas outlet side header 11 having the gas outlet port 9 are liquid-tightly attached to the housing 2. These headers may be formed of any material, and can be formed of a hydrophobic synthetic resin used for the housing described above, for example. The header may be attached by any method. For example, the header can be attached to the housing 2 by fusion bonding using ultrasound waves, high frequency waves, induction heating, and the like, by adhesion with an adhesive, or by mechanical engagement. In addition, the attachment may be performed by using a fastening ring (not shown). It is exemplary that the entire blood contact portion of the hollow fiber membrane type artificial lung 1 (the inside surface of the housing 2, the outside surfaces of the hollow fiber membranes 3) is formed of a hydrophobic material.

As shown in FIG. 2, the polymer 18 coats at least the outer surface $3a'$ (and optionally, the outer surface layer $3a$) of the hollow fiber membrane 3 which serves as the blood contact portion of the hollow fiber membrane type artificial lung 1. As described above, it is exemplary that no substantial polymer exists on the internal layer $3b$ or the inner surface layer $3c$ of the hollow fiber membrane. In the case no substantial polymer exists, hydrophobic properties of the base material itself of the membrane are maintained as they are on the internal layer or the inner surface layer of the hollow fiber membrane, and therefore the leakage of blood plasma components can be effectively prevented. For example, it is exemplary that no substantial polymer exists on both the internal layer $3b$ and the inner surface layer $3c$ of the hollow fiber membrane. Furthermore, the hollow fiber membrane 3 includes, in the center, a passage (lumen) $3d$ forming the gas chamber. In addition, the hollow fiber membrane 3 includes an opening portion $3e$ through which the outer surface $3a'$ thereof and the inner surface $3c'$ communicate with each other. In the hollow fiber membrane having such a configuration, the blood comes into contact with outer surface $3a'$ coated with the polymer 18. Meanwhile, the oxygen-containing gas flows and contacts the inner surface $3c'$. In one embodiment utilizing an outside flow type artificial lung, the hollow fiber membranes 3 include the inner surfaces $3c'$ forming the lumens where the oxygen-containing gas flows; the outer surfaces $3a'$ contact the blood; the outer surfaces $3a'$ are coated with the polymer. In one embodiment utilizing an inside flow type artificial lung, the hollow fiber membranes 3 include the inner surfaces $3c'$ forming the lumens where the blood flows; the outer surfaces $3a'$ contact the flow of oxygen-containing gas; the inner surfaces $3c'$ are coated with the coating containing the polymer.

In one aspect, the polymer coat is selectively formed on the outer surfaces (outside flow type) or the inner surfaces (inside flow type) of the hollow fiber membranes. For this reason, the blood (for example, blood plasma components) is unlikely to or does not penetrate into the inside of the fine holes of the hollow fiber membranes. Therefore, it is possible to effectively suppress or prevent blood (for example, blood plasma components) leakage from the hollow fiber membranes. For example, in a case where no substantial polymer according to one aspect of the present disclosure exists on the internal layers $3b$ of the hollow fiber membranes and the inner surface layers $3c$ of the hollow fiber membranes, the hydrophobic state of the material is maintained on the internal layers $3b$ of the hollow fiber membranes and the inner surface layers $3c$ of the hollow fiber membranes. Therefore, a large amount of blood (for example, blood plasma components) leakage can be further effectively suppressed or prevented. Accordingly, in an exemplary artificial lung, a high level of gas exchange capacity can be maintained for a long period of time.

In addition, the polymer coating can be uniformly formed on the outer surfaces or the inner surfaces of the hollow fiber membranes. For example, adhesion, attachment, and activation of the platelets are reduced on the blood contact portions of the hollow fiber membranes. Furthermore, separation of the coating from the hollow fiber membranes can be suppressed or prevented.

For example, the polymer coating is formed on the outer surfaces or the inner surfaces of the hollow fiber membranes of the artificial lung. The coating may be formed on another constituent member (for example, on the entire blood contact portion) in addition to the outer surfaces or the inner surfaces. Adhesion, attachment, and activation of the platelets can be further effectively suppressed or prevented in the entire blood contact portion of the artificial lung. In addition, since a contact angle of the blood contact surface decreases, this can facilitate a priming operation. In an exemplary embodiment, the polymer coating according to one aspect of the present disclosure can be formed on the other constituent member in contact with the blood. For example, the polymer does not coat a portion other than the blood contact portions of the hollow fiber membranes, or on another portion of the hollow fiber membranes (for example, a portion buried in the partition walls). Such a portion is not in contact with the blood, and therefore the polymer not being coated thereon does not cause a particular problem.

In an exemplary embodiment, the hollow fiber membranes are for accommodating a flow of an oxygen-containing gas inside the lumens, and the outer surfaces of the hollow fiber membranes are for contacting blood, and the outer surfaces are coated with the polymer-containing solution. In an exemplary embodiment, the hollow fiber membranes are for accommodating blood inside the lumens, and the outer surfaces of the hollow fiber membranes are for contacting a flow of an oxygen-containing gas, and the inner surfaces are coated with the polymer-containing solution.

In addition, the artificial lung may be a type shown in FIG. 3. FIG. 3 is a cross-sectional view showing another embodiment of the artificial lung. Furthermore, FIG. 4 is a cross-sectional view taken along line A-A of FIG. 3.

In FIG. 3, an artificial lung 20 includes an inner tubular member 31 having a blood circulation opening 32 on a side surface thereof, a tubular hollow fiber membrane bundle 22 having the large number of porous hollow fiber membranes 3 for gas exchange and wound around an outside surface of the inner tubular member 31, a housing 23 accommodating the tubular hollow fiber membrane bundle 22 together with the inner tubular member 31, partition walls 25 and 26 fixing both end portions of the tubular hollow fiber membrane bundle 22 within the housing in a state where both the ends of the hollow fiber membranes 3 are open, a blood inlet port 28 and blood outlet ports 29a and 29b communicating with a blood chamber 17 formed in the housing 23, and a gas inlet port 24 and a gas outlet port 27 communicating with the insides of the hollow fiber membranes 3.

Figure 4:
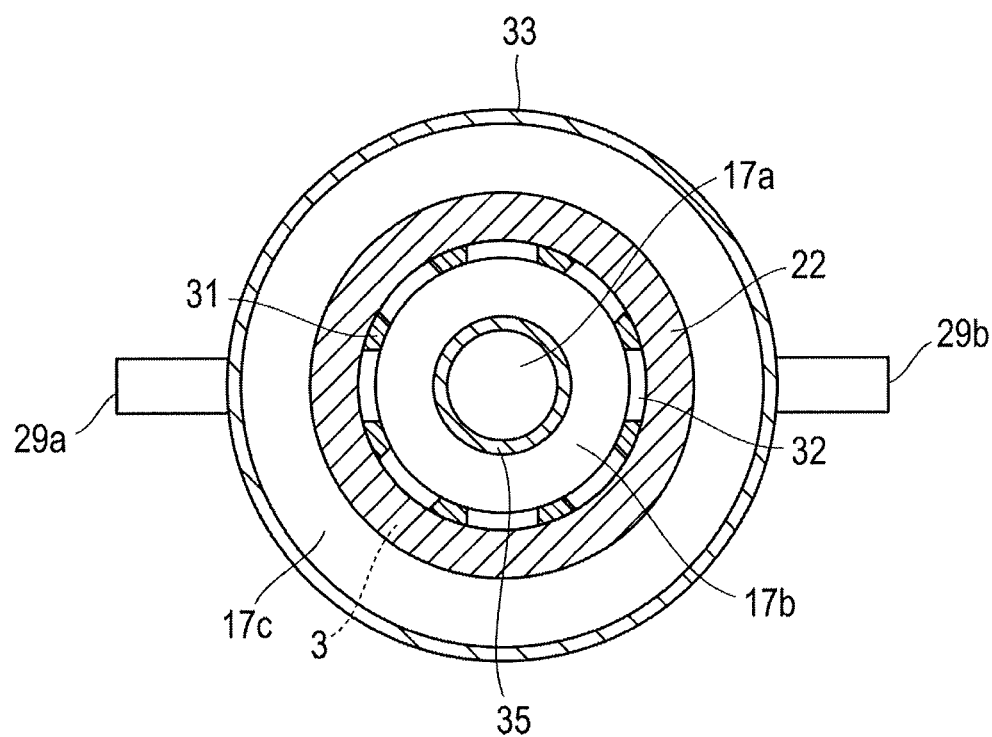
FIG. 4 is a cross-sectional view taken along line A-A of FIG. 3, according to one aspect.

In the artificial lung 20 of the present embodiment, as shown in FIG. 3 and FIG. 4, the housing 23 has an outer tubular member 33 accommodating the inner tubular member 31, the tubular hollow fiber membrane bundle 22 is accommodated between the inner tubular member 31 and the outer tubular member 33. The housing 23 has one of the blood inlet port or the blood outlet port communicating with the inside of the inner tubular member, and the other one of the blood inlet port or the blood outlet port communicating with the inside of the outer tubular member.

In the artificial lung 20 of the present embodiment, the housing 23 has an inner tubular body 35 that is accommodated in the outer tubular member 33 and the inner tubular member 31, and in which a distal end thereof is open in the inner tubular member 31. The blood inlet port 28 is formed on one end (lower end) of the inner tubular body 35, and the two blood outlet ports 29a and 29b extending outwards are formed on a side surface of the outer tubular member 33. There may be one or a plurality of the blood outlet ports.

The tubular hollow fiber membrane bundle 22 is wound around the outside surface of the inner tubular member 31. That is, the inner tubular member 31 is a core of the tubular hollow fiber membrane bundle 22. A distal end portion of the inner tubular body 35 accommodated inside the inner tubular member 31 is open in the vicinity of the first partition walls 25. In addition, the blood inlet port 28 is formed on a protruding lower end portion by the inner tubular member 31.

Each of the inner tubular body 35, the inner tubular member 31 where the hollow fiber membrane bundle 22 is wound around the outside surface thereof, and the outer tubular member 33 is arranged almost concentrically. One end (upper end) of the inner tubular member 31 where the hollow fiber membrane bundle 22 is wound around the outside surface thereof, and one end (upper end) of the outer tubular member 33 maintain the concentric positional relationship between each other by the first partition walls 25, and are in the liquid-tight state where a space formed between the inside of the inner tubular member 31, and the outer tubular member 33 and the outside surfaces of the hollow fiber membrane bundle 22 does not communicate with the outside.

Furthermore, a portion that is in a slightly upper position than the blood inlet port 28 of the inner tubular body 35, the other end (lower end) of the inner tubular member 31 where the hollow fiber membrane bundle 22 is wound around the outside surface thereof, and the other end (lower end) of the outer tubular member 33 maintain the concentric positional relationship between each other by the second partition walls 26. The above components are in a liquid-tight state where a space formed between the inside of the inner tubular member 31 and the inner tubular body 35, and a space formed between the outside surfaces of the hollow fiber membrane bundle 22 and the outer tubular member 33 do not communicate with the outside. Furthermore, the partition walls 25 and 26 are formed by a potting agent such as polyurethane and silicone rubber.

The artificial lung 20 of the present embodiment includes a blood inlet portion 17a formed by the inside of the inner tubular body 35, a first blood chamber 17b that is a substantially tubular space formed between the inner tubular body 35 and the inner tubular member 31, and a second blood chamber 17c that is a substantially tubular space formed between the hollow fiber membrane bundle 22 and the outer tubular member 33, and thereby the blood chamber 17 is formed.

The blood flowing from the blood inlet port 28 flows into the blood inlet portion 17a, moves up in the inner tubular body 35 (blood inlet portion 17a), flows out from an upper end 35a (opening end) of the inner tubular body 35, flows into the first blood chamber 17b, passes through an opening 32 formed in the inner tubular member 31, comes into contact with the hollow fiber membrane bundle 22, and after gas exchange, flows into the second blood chamber 17c, and flows out from the blood outlet ports 29a and 29b.

Furthermore, a gas inlet member 41 having the gas inlet port 24 is fixed to one end of the outer tubular member 33, and similarly, a gas outlet member 42 having the gas outlet port 27 is fixed to the other end of the outer tubular member 33. The blood inlet port 28 of the inner tubular body 35 protrudes through the gas outlet member 42.

The outer tubular member 33 is not particularly limited, and a member having a tubular body, a polygonal tube, an elliptical shape in the cross section, and the like can be used. The member can be the tubular body. Furthermore, an inner diameter of the outer tubular member is not particularly limited, and the inner diameter of the outer tubular member can be any diameter suitable for use in an artificial lung. The diameter can be approximately 32 to 164 mm. Furthermore, an effective length of the outer tubular member (that is, the portion of the length of the outer tubular member that is not buried in the partition walls) is not particularly limited, and the length can be any effective length of the outer tubular member suitable for use in an artificial lung. The effective length of the outer tubular member can be approximately 10 to 730 mm.

Furthermore, a shape of the inner tubular member 31 is not particularly limited, and for example, a member having a tubular body, a polygonal tube, an elliptical shape in a cross section, and the like can be used. The shape can be the tubular body. Furthermore, an outer diameter of the inner tubular member is not particularly limited, and the outer diameter can be any outer diameter of the inner tubular member suitable for use in an artificial lung. The outer diameter can be approximately 20 to 100 mm. Furthermore, the effective length of the inner tubular member (that is, the portion of the length of the inner tubular member that is not buried in the partition walls) is not particularly limited, and the length can be any effective length of the inner tubular member suitable for use in an artificial lung. The effective length of the inner tubular member can be approximately 10 to 730 mm.

Figure 5:
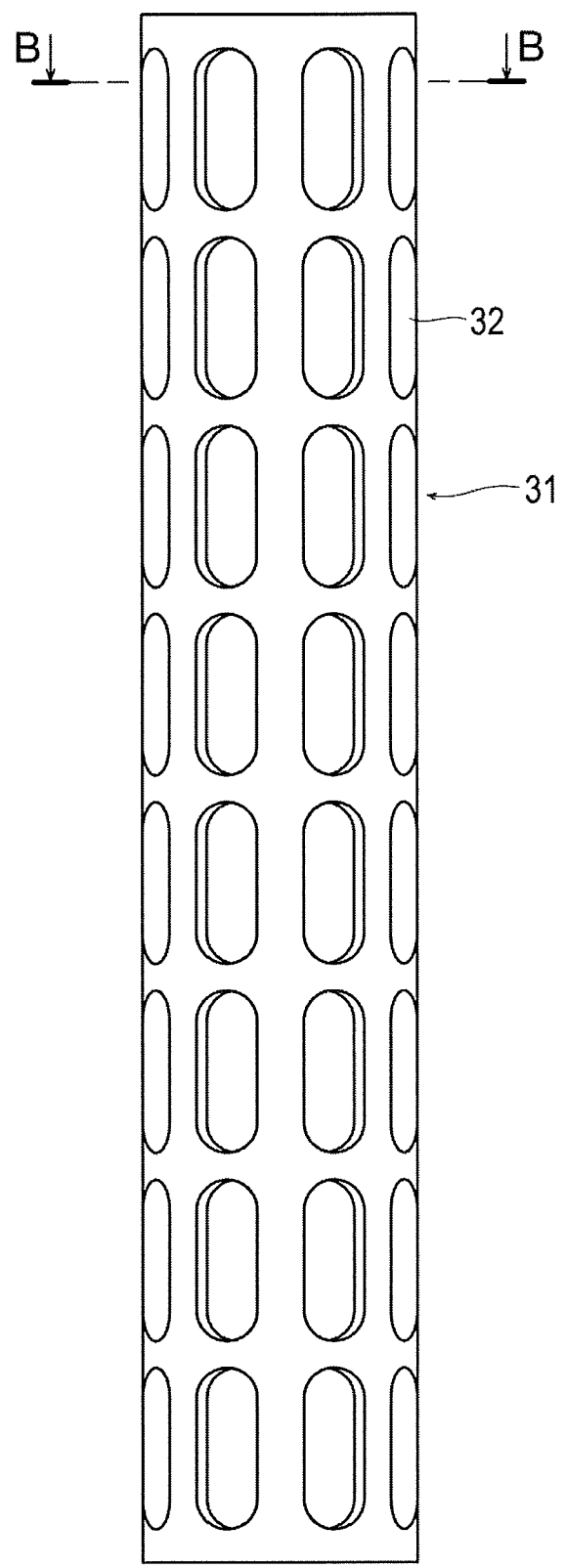
FIG. 5 is a front view showing an example of the inner tubular member used for the hollow fiber membrane artificial lung of an outside blood flow type, according to one aspect.
Figure 6:
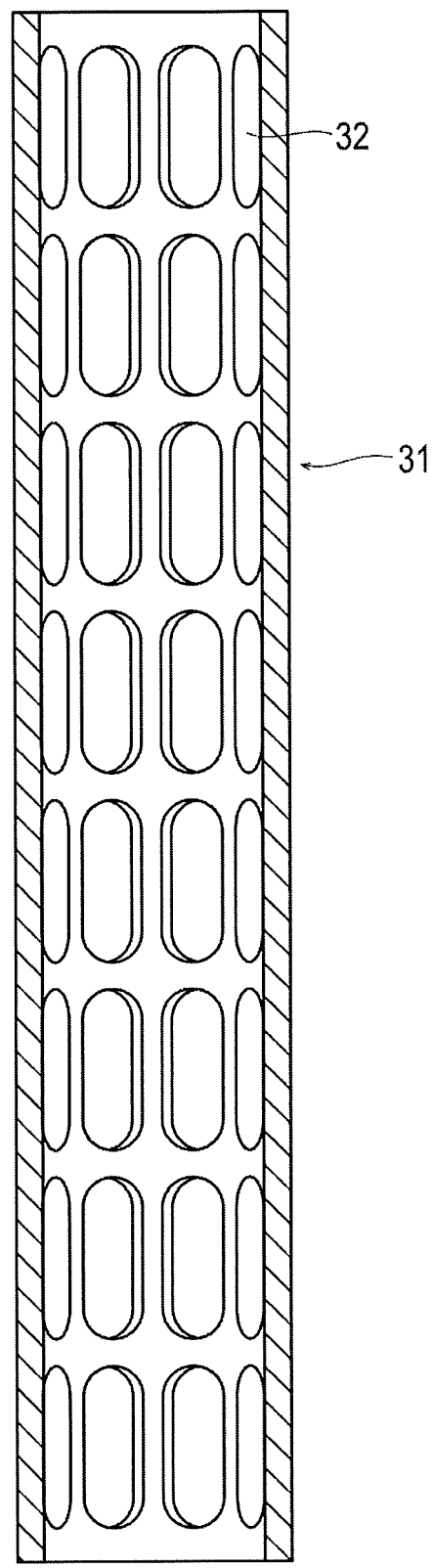
FIG. 6 is a central longitudinal cross-sectional view of the inner tubular member shown in FIG. 5, according to one aspect.
Figure 7:
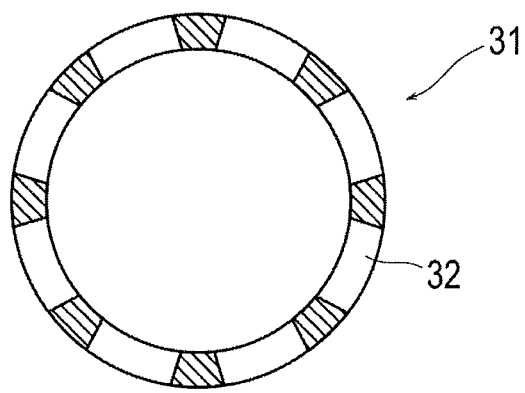
FIG. 7 is a cross-sectional view taken along line B-B of FIG. 5, according to one aspect.

The inner tubular member 31 includes a large number of blood circulation openings 32 on the side surface thereof. For example, regarding a size of the opening 32, it is exemplary that a total area is large as long as the required strength of the tubular member is maintained. As a tubular member satisfying such conditions, for example, disclosed is a tubular member having a plurality of sets of circularly arranged openings 32 in which a plurality of the openings 32 are provided on an outer peripheral surface of the inner tubular member 31. For example, the plurality of sets of circularly arranged openings can constitute 8 sets. For example, each set can include 4 to 24 openings. For example, 8 openings can be arranged in a longitudinal direction. The openings 32 can be provided at an equal angle and interval. The openings 32 can be provided in the axial direction of the tubular member at an equal interval. Exemplary blood circulation openings 32 are shown in FIG. 5 that is a front view, FIG. 6 that is a central longitudinal cross-sectional view of FIG. 5, and FIG. 7 that is a cross-sectional view taken along line B-B of FIG. 5. Furthermore, an opening shape may be a circle, a polygon, an ellipse, and the like, but an oval shape can be favorable as shown in FIG. 5.

In addition, a shape of the inner tubular body 35 is not particularly limited, and for example, a body having a tubular body, a polygonal tube, an elliptical shape in the cross section, and the like can be used. The inner tubular body can be a tubular body. Furthermore, a distance between a distal end opening of the inner tubular body 35 and the first partition walls 25 is not particularly limited, and any distance suitable for use in an artificial lung can be applied. The distance can be approximately 20 to 50 mm. Furthermore, an inner diameter of the inner tubular body 35 is not particularly limited, and the inner diameter can be any inner diameter of the inner tubular body suitable for use in an artificial lung. The inner diameter of the inner tubular body can be approximately 10 to 30 mm.

A thickness of the tubular hollow fiber membrane bundle 22 is not particularly limited, and the thickness can be any thickness of the tubular hollow fiber membrane bundle suitable for use in an artificial lung. The thickness can be 5 to 35 mm, for example, 10 mm to 28 mm. Furthermore, a filling rate of the hollow fiber membranes with respect to the tubular space formed by a space between the outside surface of the tubular hollow fiber membrane bundle 22 and the inside surface is not particularly limited, and the filling rate can be any filling rate suitable for use in an artificial lung. The filling rate can be 40% to 85%, for example, 45% to 80%. Furthermore, an outer diameter of the hollow fiber membrane bundle 22 can be any outer diameter of the hollow fiber membrane bundle suitable for use in an artificial lung. The outer diameter of the hollow fiber membrane bundle can be 30 to 170 mm, for example, 70 to 130 mm. As a gas exchange membrane, the membrane described above is used.

The hollow fiber membrane bundle 22 can be formed by winding the hollow fiber membranes around the inner tubular member 31, for example, using the inner tubular member 31 as a core, forming a hollow fiber membrane bobbin, fixing both ends of the formed hollow fiber membrane bobbin by the partition walls, and then cutting both the ends of the hollow fiber membrane bobbin together with the inner tubular member 31 that is a core. The hollow fiber membranes become open on the outside surface of the partition walls by this cutting. A method for forming hollow fiber membranes is not limited to the above method, and any suitable method for forming hollow fiber membranes can be used or appropriately modified for use.

For example, it is exemplary that one or a plurality of the hollow fiber membranes are wound around the inner tubular member 31 substantially in parallel at the same time such that adjacent hollow fiber membranes have a substantially constant interval. Therefore, blood drift can be more effectively suppressed. In addition, a distance between the hollow fiber membrane and an adjacent hollow fiber membrane is not limited to the following, but the distance can be ¹/₁₀ to 1/1 of the outer diameter of the hollow fiber membranes. Furthermore, the distance between the hollow fiber membrane and an adjacent hollow fiber membrane can be 30 to 200 μm, for example, 50 to 180 μm.

Furthermore, it is exemplary that the hollow fiber membrane bundle 22 is formed by one or a plurality (for example, 2 to 16 membranes) of the hollow fiber membranes being wound around the inner tubular member 31 at the same time such that all adjacent hollow fiber membranes have a substantially constant interval. For example, the hollow fiber membrane bundle 22 can be formed by the hollow fiber membranes being wound around the inner tubular member 31 according to movement of a rotator for rotating the inner tubular member 31 and a winder for interweaving the hollow fiber membranes under the condition in Expression (1) when winding the hollow fiber membranes around the inner tubular member.

$$\text{traverse [mm/lot]} \times n \text{ (integer)} = \text{traverse amplitude} \times 2 \pm \text{(outer diameter of fiber+interval)} \times \text{the number of windings} \quad \text{Expression (1):}$$

It is possible to further reduce the formation of blood drift by setting the condition as above. The variable n in Expression (1) represents a ratio between the number of rotations of the rotator for winding and the number of reciprocations of the winder at this time, and is not particularly limited, but is generally 1 to 5 (i.e., 1:1 to 5:1), for example, 2 to 4 (i.e., 2:1 to 4:1).

The artificial lung according to another embodiment above is a type in which the blood flows from the inside of the tubular hollow fiber membrane bundle 22, and after passing through the hollow fiber membrane bundle 22, flows to the outside of the hollow fiber membrane bundle 22, and then flows out from the artificial lung 20, but the lung is not limited thereto. The artificial lung may be a type in which the blood flows from the outside of the tubular hollow fiber membrane bundle 22, and after passing through the hollow fiber membrane bundle 22, flows to the inside of the hollow fiber membrane bundle 22, and then flows out from the artificial lung 20.

Furthermore, also in the hollow fiber membrane type artificial lung 20, it is exemplary that the polymer 18 according to one aspect of the present disclosure coats at least the outer surface 3a' (and optionally, outer surface layer 3a) of the hollow fiber membrane 3 of this hollow fiber membrane type artificial lung 1, as shown in FIG. 2. Here, the polymer according to one aspect of the present disclosure may exist on the internal layer 3b or the inner surface layer 3c of the hollow fiber membrane 3, but it is exemplary that no substantial polymer according to one aspect of the present disclosure exists on the internal layer 3b or the inner surface layer 3c of the hollow fiber membrane 3. In addition, the hollow fiber membrane 3 includes, in the center, the passage 3d forming the gas chamber. The preferred aspect of the hollow fiber membranes (inner diameter, outer diameter, wall thickness, porosity, and the like) is not particularly limited, but the same aspect as described in FIG. 1 above can be adopted.

In the artificial lung 20 according to the present embodiment, the hollow fiber membranes 3 have a bobbin shape in which membranes are in contact with each other and overlapped many times. In the present embodiment, the polymer coating is selectively and uniformly formed on the outer surfaces or the inner surfaces of the hollow fiber membranes. The leakage of blood (for example, blood plasma components) to the inner surface layers of the hollow fiber membranes can be suppressed or prevented. That is, the leakage of blood (for example, blood plasma components) can be effectively suppressed or prevented by the polymer selectively coating the outer surfaces 3a' (and optionally, outer surface layers 3a) of the hollow fiber membranes 3, which are the blood contact portions. For example, in a case where no substantial polymer according to one aspect of the present disclosure exists on the internal layers 3b of the hollow fiber membranes and the inner surface layers 3c of the hollow fiber membranes, the hydrophobic state of the material is maintained on the internal layers 3b of the hollow fiber membranes and the inner surface layers 3c of the hollow fiber membranes, and therefore a large amount of blood (for example, blood plasma components) leakage can be further effectively suppressed or prevented. In the present embodiment, the blood flow path is complicated and has many narrow portions, which is excellent for the gas exchange capacity, but the adhesion, attachment, and activation of the platelets deteriorate in some cases compared to the artificial lung of an outside blood flow type which is not a bobbin type. However, as described above, since the polymer coating is uniform, the adhesion, attachment, and activation of the platelets in the blood contact portions of the hollow fiber membranes occur less. Furthermore, separation of the coating from the hollow fiber membranes (for example, a portion where coating is uneven) can be suppressed or prevented.

The polymer coating according to the present embodiment is formed on the outer surfaces or the inner surfaces of the hollow fiber membranes of the artificial lung. The coating may be formed on another constituent member (for example, on the entire blood contact portion) in addition to the outer surfaces or the inner surfaces. Adhesion, attachment, and activation of the platelets can be further effectively suppressed or prevented in the entire blood contact portion of the artificial lung. In addition, since a contact angle of the blood contact surface decreases, this can facilitate a priming operation. In an exemplary embodiment, the polymer coating according to one aspect of the present disclosure can be formed on the other constituent member in contact with the blood. For example, the polymer does not coat a portion other than the blood contact portions of the hollow fiber membranes, or another portion of the hollow fiber membranes (for example, a portion buried in the partition walls, and a contact portion of the hollow fiber). Such a portion is not in contact with the blood, and therefore not coating the polymer thereon does not cause a particular problem.

<Polymer (Alkoxyalkyl (Meth)Acrylate Polymer) According to One Aspect of the Present Disclosure>

The polymer according to one aspect of the present disclosure has a structural unit derived from alkoxyalkyl (meth)acrylate represented by Formula (I):

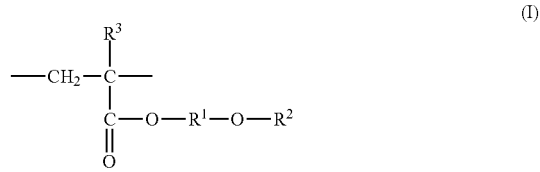

The polymer according to one aspect of the present disclosure has, for example, excellent antithrombotic activity and biocompatibility. Note that in the present specification, "(meth)acrylate" means "acrylate and/or methacrylate". That is, "alkoxyalkyl (meth)acrylate" includes all cases of only alkoxyalkyl acrylate, only alkoxyalkyl methacrylate, and alkoxyalkyl acrylate and alkoxyalkyl methacrylate.

In General Formula 1, $R^1$ represents an alkylene group having 1 to 4 carbon atoms. The alkylene group having 1 to 4 carbon atoms is not particularly limited, and includes a linear or a branched alkylene group of a methylene group, an ethylene group, a trimethylene group, a tetramethylene group, and a propylene group. Among these, an ethylene group and a propylene group are exemplary, and in consideration of further enhanced effects of antithrombotic activity and biocompatibility, an ethylene group is exemplary. $R^2$ represents an alkyl group having 1 to 4 carbon atoms. The alkyl group having 1 to 4 carbon atoms is not particularly limited, and includes a linear or a branched alkyl group of a methyl group, an ethyl group, a propyl group, an isopropyl group, a butyl group, an isobutyl group, a sec-butyl group, and a tert-butyl group. Among these, a methyl group and an ethyl group are exemplary, and in consideration of further enhanced effects of antithrombotic activity and biocompatibility, a methyl group is exemplary. $R^3$ represents a hydrogen atom or a methyl group. In a case where the polymer according to one aspect of the present disclosure has two or more of structural units derived from alkoxyalkyl (meth) acrylate, each structural unit may be the same or different from each other.

Specific examples of alkoxyalkyl (meth)acrylate include methoxymethyl acrylate, methoxyethyl acrylate, methoxypropyl acrylate, ethoxymethyl acrylate, ethoxyethyl acrylate, ethoxypropyl acrylate, ethoxybutyl acrylate, propoxymethyl acrylate, butoxyethyl acrylate, methoxybutyl acrylate, methoxymethyl methacrylate, methoxyethyl methacrylate, ethoxymethyl methacrylate, ethoxyethyl methacrylate, propoxymethyl methacrylate, butoxyethyl methacrylate, and the like. Among these, from the viewpoint of further enhanced effects of antithrombotic activity and biocompatibility, methoxyethyl (meth)acrylate and methoxybutyl acrylate are exemplary, and methoxyethyl acrylate (MEA) is exemplary. That is, the polymer according to one aspect of the present disclosure can be polymethoxyethyl acrylate (PMEA). The above alkoxyalkyl (meth)acrylate may be used alone or as a mixture of two or more kinds thereof.

The polymer according to one aspect of the present disclosure has a structural unit derived from alkoxyalkyl (meth)acrylate, and may be a polymer (homopolymer) having one or two or more of structural units derived from alkoxyalkyl (meth)acrylate, or may be a polymer (copolymer) having one or two or more of structural units derived from alkoxyalkyl (meth)acrylate, and having one or two or more of structural units (other structural units) derived from a monomer copolymerizable with the alkoxyalkyl (meth)acrylate. In a case where the polymer according to one aspect of the present disclosure has two or more of the structural units, the structure of the polymer (copolymer) is not particularly limited, and may be any one of a random copolymer, an alternating copolymer, a periodic copolymer, or a block copolymer. In addition, the end of the polymer is not particularly limited and is appropriately determined according to the type of raw material being used, and can be a hydrogen atom.

In a case where the polymer according to one aspect of the present disclosure has structural units other than the structural units derived from alkoxyalkyl (meth)acrylate, a monomer copolymerizable with the alkoxyalkyl (meth)acrylate (copolymerizable monomer) is not particularly limited. Examples thereof include methyl acrylate, ethyl acrylate, propyl acrylate, butyl acrylate, 2-ethylhexyl acrylate, methyl methacrylate, ethyl methacrylate, propyl methacrylate, butyl methacrylate, 2-ethylhexyl methacrylate, hexyl acrylate, hexyl methacrylate, ethylene, propylene, acrylamide, N,N-dimethylacrylamide, N,N-diethylacrylamide, aminomethyl acrylate, aminoethyl acrylate, aminoisopropyl acrylate, diaminomethyl acrylate, diaminoethyl acrylate, diaminobutyl acrylate, methacrylamide, N,N-dimethylmethacrylamide, N,N-diethyl methacrylamide, aminomethyl methacrylate, aminoethyl methacrylate, diaminomethyl methacrylate, diaminoethyl methacrylate, and the like. Among these, as a copolymerizable monomer, a monomer not having a hydroxyl group or a cationic group in the molecule is exemplary. The copolymer may be any one of a random copolymer, a block copolymer, or a graft copolymer, and can be synthesized by any suitable method such as radical polymerization, ionic polymerization, and polymerization using a macromer. In all structural units of the copolymer, a ratio of the structural units derived from a copolymerizable monomer is not particularly limited, but in consideration of antithrombotic activity and biocompatibility, and the like, it is exemplary that the structural units derived from a copolymerizable monomer (the other structural units) are more than 0% by mole and 50% by mole or less with respect to all structural units of the copolymer. If the units are more than 50% by mole, there is a possibility that the effect of alkoxyalkyl (meth)acrylate deteriorates.

In addition, a weight average molecular weight of the polymer according to one aspect of the present disclosure is not particularly limited, but can be 80,000 or more. If using the polymer having this weight average molecular weight, the leakage of blood plasma components (blood plasma leakage) can be sufficiently suppressed even in the thin-walled hollow fiber membranes. Meanwhile, as described above, the content of the polymer of a low molecular weight in the coating can be reduced by increasing the molecular weight of the polymer. With this molecular weight, the elution of the coating (for example, the polymer of a low molecular weight) into blood can be suppressed or prevented. From the viewpoint of the elution of the coating (for example, the polymer of a low molecular weight) into blood being further suppressed or prevented, the weight average molecular weight of the polymer according to one aspect of the present disclosure can be 250,000 to 600,000, for example, 300,000 to 500,000. In a case where the weight average molecular weight is within the above range, the elution of the coating (for example, the polymer of a low molecular weight) into blood can be further effectively suppressed or prevented. For this reason, even the artificial lung including the hollow fiber membranes of which the surface is coated with the coat having such a polymer in a low concentration can exhibit and maintain excellent antithrombotic activity. Furthermore, it is also exemplary in terms of antithrombotic activity and biocompatibility. Note that in a case where the weight average molecular weight of the polymer according to one aspect of the present disclosure is excessively high, the polymer in the polymer-containing solution is likely to aggregate or be precipitated, and there is a possibility that it is difficult to prepare a stable polymer-containing solution. Furthermore, in the present specification, "the polymer of a low molecular weight" means a polymer having a weight average molecular weight of less than 100,000.

In the present specification, the "weight average molecular weight" is a weight obtained by adopting a value measured by gel permeation chromatography (GPC) using polystyrene as a standard substance and tetrahydrofuran (THF) as a mobile phase, respectively. Specifically, the polymer is dissolved in tetrahydrofuran (THF) to become a concentration of 10 mg/ml, and therefore a sample is prepared. Regarding the sample prepared as above, GPC column LF-804 (manufactured by Shodex) is attached to a GPC system LC-20 (manufactured by Shimadzu Corporation), THF is allowed to flow as a mobile phase, and polystyrene is used as a standard substance to measure GPC of the polymer. After preparing a calibration curve with a standard polystyrene, the weight average molecular weight of the polymer is calculated based on this curve.

In addition, the polymer according to one aspect of the present disclosure can be produced by any suitable method.

For example, a method can be used, in which one or two or more monomers (copolymerizable monomer) copolymerizable with alkoxyalkyl (meth)acrylate represented by Formula (II) and with the above alkoxyalkyl (meth)acrylate if necessary, are stirred in a polymerization solvent together with a polymerization initiator to prepare a monomer solution, and by heating the above monomer solution, alkoxyalkyl (meth)acrylate or alkoxyalkyl (meth)acrylate and a copolymerizable monomer if necessary are (co)polymerized.

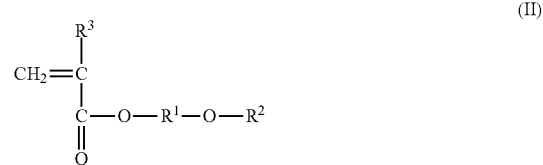

(II)

In Formula (II), substituents $R^1$, $R^2$ and $R^3$ can be the same as those defined in Formula (I).

The polymerization solvent that can be used in the above preparation of the monomer solution is not particularly limited. The solvent is capable of dissolving the alkoxyalkyl (meth)acrylate of Formula (II) and if necessary, a copolymerizable monomer. Examples thereof include water, alcohols such as methanol, ethanol, propanol and isopropanol; aqueous solvents such as polyethylene glycols; aromatic solvents such as toluene, xylene and tetralin; halogenated solvents such as chloroform, dichloroethane, chlorobenzene, dichlorobenzene, trichlorobenzene; and the like. Among these, in consideration of alkoxyalkyl (meth)acrylate being easily dissolved and the polymer that has the above weight average molecular weight being easily obtained, methanol is exemplary. A monomer concentration in the monomer solution is not particularly limited, but the weight average molecular weight of the polymer obtained can be increased by setting the concentration relatively high. For this reason, in consideration of the polymer that has the above weight average molecular weight being easily obtained, and the like, the monomer concentration in the monomer solution can be 15% to 60% by weight, for example, 20% to 50% by weight, for example, 25% to 45% by weight. In a case of using alkoxyalkyl (meth)acrylate and a copolymerizable monomer, the above monomer concentration means a total concentration of these monomers.

The polymerization initiator is not particularly limited and any suitable initiator may be used. The initiator can be a radical polymerization initiator in terms of being excellent in polymerization stability, and examples thereof include persulfates such as potassium persulfate (KPS), sodium persulfate and ammonium persulfate; peroxides such as hydrogen peroxide, t-butyl peroxide and methyl ethyl ketone peroxide; and azo compounds such as azobisisobutyronitrile (AIBN), 2,2'-azobis(4-methoxy-2,4-dimethylvaleronitrile), 2,2'-azobis(2,4-dimethylvaleronitrile), 2,2'-azobis[2-(2-imidazolin-2-yl)propane]dihydrochloride, 2,2'-azobis[2-(2-imidazolin-2-yl)propane]disulfate dihydrate, 2,2'-azobis(2-methylpropionamidine)dihydrochloride, 2,2'-azobis[N-(2-carboxyethyl)-2-methylpropionamidine)] hydrate, 3-hydroxy-1,1-dimethylbutyl peroxyneodecanoate, α-cumyl peroxyneodecanoate, 1,1,3,3-tetrabutyl peroxyneodecanoate, t-butyl peroxyneodecanoate, t-butyl peroxyneoheptanoate, t-butyl peroxypivalate, t-amyl peroxyneodecanoate, t-amyl peroxypivalate, di(2-ethylhexyl) peroxydicarbonate, di(secondary butyl)peroxydicarbonate, and azobiscyanovaleric acid. For example, a reducing agent such as sodium sulfite, sodium hydrogen sulfite, and ascorbic acid may be used in combination with the above radical polymerization initiators as a redox type initiator. A blending amount of the polymerization initiators can be 0.0001 to 1% by mole with respect to a total amount of the monomer. Alternatively, the blending amount of the polymerization initiators can be 0.005 to 2 parts by weight, for example, 0.05 to 0.5 parts by weight with respect to 100 parts by weight of monomer (a total weight in a case of using a plurality types of monomers). With such a blending amount of the polymerization initiators, the polymer having a desired weight average molecular weight can be efficiently produced.

The above polymerization initiator as it is may be mixed with the monomers (for example, alkoxyalkyl (meth)acrylate or alkoxyalkyl (meth)acrylate and the copolymerizable monomer) and the polymerization solvent. The initiator in a solution state obtained by the initiator dissolved in another solvent in advance, may be mixed with the monomers and the polymerization solvent. In the latter case, the solvent used to dissolve the polymerization initiator is not particularly limited, as long as the polymerization initiator can be dissolved in the solvent. The solvent used to dissolve the polymerization initiator can be selected from the above polymerization solvents. Furthermore, the solvent used to dissolve the polymerization initiator may be the same as or different from the above polymerization solvent, but can be a solvent that is the same as the above polymerization solvent in consideration of the ease of control of polymerization, and the like. Furthermore, in this case, a concentration of the polymerization initiator in the solvent used to dissolve the polymerization initiator is not particularly limited, but an addition amount of the polymerization initiator can be 0.1 to 10 parts by weight, for example, 0.5 to 5 parts by weight with respect to 100 parts by weight of the solvent used to dissolve the polymerization initiator in consideration of the ease of mixing, and the like.

In a case of using the polymerization initiator in the solution state, deaeration treatment may be performed in advance before adding a solution in which the monomers (alkoxyalkyl (meth)acrylate or alkoxyalkyl (meth)acrylate and the copolymerizable monomer) are dissolved in the polymerization solvent, to the polymerization initiator solution. For the deaeration treatment, for example, an inert gas such as nitrogen gas or argon gas may be bubbled for approximately 0.5 to 5 hours with a methanol solution. In the deaeration treatment, the methanol solution may be adjusted to approximately 30° C. to 80° C., for example, to a polymerization temperature in a polymerization process described below.

Next, the above monomer solution is heated, and thus alkoxyalkyl (meth)acrylate or alkoxyalkyl (meth)acrylate and the other monomer are (co)polymerized. As a polymerization method, for example, any suitable polymerization method such as radical polymerization, anionic polymerization, and cationic polymerization can be adopted, and radical polymerization which facilitates production can be used.

Polymerization conditions are not particularly limited, as long as the above monomers (alkoxyalkyl (meth)acrylate or alkoxyalkyl (meth)acrylate and the copolymerizable monomer) can be polymerized under the conditions. For example, the polymerization temperature can be 30° C. to 80° C., for example, 40° C. to 55° C. The polymerization time can be 1 to 24 hours, for example, 5 to 12 hours. Under such conditions described above, a polymer having a high molecular weight as above can be further efficiently produced. In addition, it is possible to effectively suppress or prevent gelation in the polymerization process and to achieve high production efficiency.

In addition, a chain transfer agent, a polymerization rate-adjusting agent, a surfactant, and other additives may be appropriately used during polymerization if desired.

An atmosphere under which the polymerization reaction is carried out is not particularly limited, and the reaction may be carried out under an air atmosphere, an inert gas atmosphere such as nitrogen gas or argon gas, and the like. In addition, during the polymerization reaction, the reaction solution may be stirred.

The polymer after polymerization can be purified by a general purification method such as a reprecipitation method, a dialysis method, an ultrafiltration method, and an extraction method.

The purified polymer can be dried by an arbitrary method such as freeze drying, reduced pressure drying, spray drying, and heat drying, but freeze drying or reduced pressure drying is exemplary from the viewpoint that the influence on the physical properties of the polymer is small.

<Method for Manufacturing Artificial Lung>

In the artificial lung according to one aspect of the present disclosure, the outer surfaces or the inner surfaces of the hollow fiber membranes are coated with a polymer-containing solution having the surface tension of 40 to 55 dyn/cm and containing the polymer according to one aspect of the present disclosure and the solvent as described above. That is, provided is a method for manufacturing an artificial lung that has a plurality of porous hollow fiber membranes for gas exchange made of a hydrophobic polymer material, in which the hollow fiber membranes have inner surfaces forming lumens and outer surfaces.

The method includes coating the inner surfaces forming the lumens of the hollow fiber membranes or the outer surfaces with a polymer-containing solution that has a surface tension of 40 to 55 dyn/cm and that contains a solvent and a polymer having a structural unit derived from alkoxyalkyl (meth)acrylate represented by Formula (I):

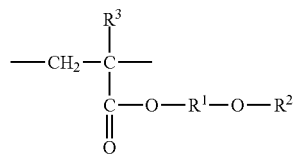

(I)

in which $R^3$ represents a hydrogen atom or a methyl group, $R^1$ represents an alkylene group having 1 to 4 carbon atoms, and $R^2$ represents an alkyl group having 1 to 4 carbon atoms.

Hereinafter, preferred aspects of the method for manufacturing an artificial lung will be described. Note that the present invention is not limited to the following preferred aspects. For example, the outer surfaces or the inner surfaces of the hollow fiber membranes are coated with the polymer-containing solution having the surface tension of 40 to 55 dyn/cm.

First, after assembling an artificial lung (for example, an artificial lung having the same structure as that of FIG. 1 or FIG. 3), the polymer-containing solution in which the polymer according to one aspect of the present disclosure is dissolved in the solvent so that the surface tension becomes 40 to 55 dyn/cm, is allowed to come into contact with the blood flowing side of the artificial lung, and thereby the inner surfaces or the outer surfaces (that is, the blood contact portions) of the hollow fiber membranes are coated with the polymer according to one aspect of the present disclosure. Alternatively, coating of the hollow fiber membranes with the polymer-containing solution may be performed before assembling the artificial lung.

The surface tension of the polymer-containing solution is 40 to 55 dyn/cm. If the above surface tension is less than 40 dyn/cm, the polymer penetrates into the inner surfaces of the fine holes of the hollow fiber membranes (surfaces on the side where the oxygen-containing gas flows). This increases a possibility of blood plasma leakage in the thin-walled hollow fiber membranes after blood circulation. If the surface tension is more than 55 dyn/cm, dispersibility of the polymer in the coating solvent deteriorates, and aggregation and the like are likely to occur, which are not preferable. From the viewpoint of suppressing or preventing the penetration of the polymer into the fine holes of the hollow fiber membranes, the surface tension of the polymer-containing solution can be 42 to 53 dyn/cm, for example, 45 to 50 dyn/cm.

In the present specification, the surface tension of the polymer-containing solution is a value measured according to the following method.

<Method for Measuring Surface Tension of Polymer-Containing Solution>

The surface tension of the polymer-containing solution is measured using a DuNouy Tensiometer (manufactured by Ito Seisakusho Co., Ltd.). Specifically, a platinum ring is suspended at the tip of a thin rod attached to the center of a steel wire and is brought into contact with a liquid surface of the polymer-containing solution at the horizontal position. A knob is turned and the steel wire is twisted to pull up the platinum ring. The instant when the platinum ring is separated from the liquid surface, the force (dyne) and distance (cm) are measured with a scale plate and a pointer. The surface tension (dyn/cm) of the polymer-containing solution is determined based on the force (dyne) and distance (cm) measured the instant when the platinum ring is separated from the liquid surface. The above method of measuring the surface tension of the polymer-containing solution is in accordance with ASTM D971.

A method for controlling the above surface tension of the polymer-containing solution is not particularly limited as long as the surface tension is within the above range. For example, (a) the concentration of the polymer according to one aspect of the present disclosure in the polymer-containing solution is controlled within an appropriate range; (b) a solvent is appropriately selected; and a method appropriately combining (a) and (b) can be applied. Among these, (a) and (b) can be applied, and the method of (b) can be applied.

Regarding (a) among the above, the concentration of the polymer according to one aspect of the present disclosure in the polymer-containing solution is not particularly limited. In consideration of the ease of forming the coat, the effect of reducing coating unevenness, and the like, the concentration can be 0.01% to 5.0% by weight, for example, 0.05% to 1.0% by weight. Note that in a case where the concentration of the polymer in the polymer-containing solution is 0.5% by weight or less, which is low, the blending amount of the polymer becomes small and the polymer hardly acts as a surfactant. In the polymer with such a low concentration, there is no substantial change in the surface tension of the polymer-containing solution (application solution). Therefore, in a case of applying the polymer-containing solution (application solution) with a low concentration on the outer surfaces or the inner surfaces of the hollow fiber membranes (that is, to form the polymer coating), it is exemplary that the solvent is appropriately selected as described below. Coating the hollow fiber membranes with the polymer-containing solution can be performed before assembling the artificial lung.

Regarding the above (b), a solvent used in preparation of the polymer-containing solution is not particularly limited as long as the solvent can dissolve the polymer according to one aspect of the present disclosure and can control the surface tension of the polymer-containing solution to 40 to 55 dyn/cm.

The solvent can contain water from the viewpoint of further effectively preventing the penetration of the polymer-containing solution up to surfaces on the side (inner surfaces or outer surfaces) of the fine holes of the hollow fiber membranes where the oxygen-containing gas flows, for example, up to a center portion of the fine holes. The solvent other than water, which is used in preparation of the polymer-containing solution, is not particularly limited, but can be methanol, acetone, and ethanol in consideration of solubility of the polymer according to the present disclosure and the ease of controlling the surface tension of the polymer-containing solution. The above solvent other than water may be used alone or in a form of a mixture of two or more kinds thereof. Among these, in consideration of further enhancement in the solubility of the polymer according to one aspect of the present disclosure and further ease of controlling the surface tension of the polymer-containing solution, the solvent can be methanol. That is, the solvent can contain water and methanol. A mixing ratio of water and methanol is not particularly limited, but in consideration of further enhancement in the solubility of the polymer according to one aspect of the present disclosure and further ease of controlling the surface tension of the polymer-containing solution, the mixing ratio (volume ratio) of water:methanol can be 5:1 to 99:1, for example, 6:1 to 49:1, for example, 7:1 to 30:1. That is, the solvent can contain water and methanol of the mixing ratio (volume ratio) of 5:1 to 99:1, for example, can contain water and methanol of the mixing ratio (volume ratio) of 6:1 to 49:1, for example, can contain water and methanol of the mixing ratio (volume ratio) of 7:1 to 30:1.

In one aspect, the outer surfaces or the inner surfaces of the hollow fiber membranes are allowed to come into contact with the polymer-containing solution (for example, the polymer-containing solution is circulated to the blood flowing side of the artificial lung), and therefore coated films of the polymer are formed on the outer surfaces or the inner surfaces of the hollow fiber membranes. An application amount of polymer-containing solution on the outer surfaces or the inner surfaces of the hollow fiber membranes is not particularly limited.

A polymer-coating method is not particularly limited, and any suitable method of the related art such as filling, dip coating (immersion method), spraying, spin coating, dropping, doctor blade, brush coating, roll coater, air knife coating, curtain coating, wire bar coating, gravure coating, and mixed solution-impregnated sponge coating can be applied.

A condition for forming the coated film of the polymer is not particularly limited. For example, contact time of the polymer-containing solution and the hollow fiber membranes (circulation time of the polymer-containing solution to the blood flowing side of the artificial lung) can be 1 to 5 minutes, for example, 1 to 3 minutes, in consideration of the ease of forming the coated film, the effect of reducing coating unevenness, and the like. In addition, a contact temperature of the polymer-containing solution and the hollow fiber membranes (circulation temperature of the polymer-containing solution to the blood flowing side of the artificial lung) can be 5° C. to 40° C., for example, 15° C. to 30° C., in consideration of the ease of forming the coated film, the effect of reducing coating unevenness, and the like.

By drying the coated film after contact with the polymer-containing solution, the coating formed of the polymer according to one aspect of the present disclosure is formed on the outer surfaces or the inner surfaces of the hollow fiber membranes. A drying condition is not particularly limited as long as it is a condition where the coating by the polymer according to one aspect of the present disclosure can be formed on the outer surfaces or the inner surfaces of the hollow fiber membranes (furthermore, on the outer surface layers), or on the inner surfaces (furthermore, on inner surface layers). For example, a drying temperature can be 5° C. to 50° C., for example, 15° C. to 40° C. In addition, drying time can be 60 to 300 minutes, for example, 120 to 240 minutes. Alternatively, the coated film may be dried by allowing a gas to continuously or gradually flow into the hollow fiber membranes, wherein the gas can be 5° C. to 40° C., for example, 15° C. to 30° C. The types of the gas are not particularly limited as long as a gas has no influence on the coated film and the coated film can be dried thereby. Specific examples thereof include air, inert gas such as nitrogen gas, argon gas, and the like. As long as the coated film can be sufficiently dried with a circulation amount of the gas, an amount thereof is not particularly limited, but can be 5 to 150 L, for example, 30 to 100 L.

According to an exemplary forming method, in a case where the coating is formed on the outer surface side of the hollow fiber membranes, the penetration of an antithrombotic material into the internal layers of the hollow fiber membranes and further to the inner surfaces is effectively suppressed or prevented, and therefore the antithrombotic material preferentially remains on the outer surfaces of the hollow fiber membranes. In a case where the coating is formed on the inner surface side of the hollow fiber membranes, the penetration of the antithrombotic material into the internal layers of the hollow fiber membranes and further to the outer surfaces is effectively suppressed or prevented, and therefore the antithrombotic material preferentially remains on the inner surface of the hollow fiber membranes.

Accordingly, in the artificial lung according to one aspect, the infiltration of blood (for example, blood plasma components) into the fine holes along the coating of the polymer occurs less or no infiltration occurs, and therefore the leakage of blood (for example, blood plasma components) can be effectively suppressed or prevented.

Specifically, in the artificial lung according to one aspect, blood plasma leakage resistance performance can be 15 mmHg or less, for example, 10 mmHg or less, for example, 8 mmHg or less. A lower limit of the blood plasma leakage resistance performance is not particularly limited because it can be exemplary if the resistance becomes lower, and a measurement limit is the lower limit. As described above, according to one aspect, it became possible for the first time that the blood plasma leakage resistance performance as described above is achieved even in the hollow fiber membranes having a thin wall thickness of 20 μm or more and less than 50 μm. That is, an exemplary aspect provides an artificial lung that has a plurality of porous hollow fiber membranes for gas exchange made of a hydrophobic polymer material, in which the hollow fiber membranes have inner surfaces forming lumens and outer surfaces, and a wall thickness between the inner surfaces and the outer surfaces is 20 μm or more and less than 50 μm.

Any one of the inner surface or the outer surface is coated with a coat that contains a polymer having a structural unit derived from alkoxyalkyl (meth)acrylate represented by Formula (I):

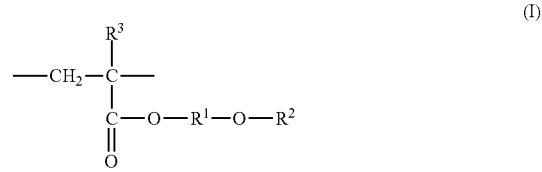

(I)

in which $R^3$ represents a hydrogen atom or a methyl group, $R^1$ represents an alkylene group having 1 to 4 carbon atoms, and $R^2$ represents an alkyl group having 1 to 4 carbon atoms, and the blood plasma leakage resistance performance is 15 mmHg or less.

A method for measuring blood plasma leakage resistance performance is described below.

If a polymer having a high molecular weight is used (for example, a weight average molecular weight is 250,000 to 600,000), the elution of a coating material into blood (for example, the polymer) can be suppressed or prevented. Specifically, an elution amount of the polymer can be 20% or less, for example, 10% or less, for example, 5% or less (lower limit: 0%). A method for measuring the elution amount of the polymer is described below.

In addition, the polymer according to one aspect of the present disclosure has excellent antithrombotic activity and biocompatibility (the suppression and prevention effects of the adhesion and attachment of the platelets and the suppression and prevention effects of the activation of the platelets) and, for example, has excellent suppression and prevention effects of the adhesion and attachment of the platelets. Therefore, the artificial lung according to one aspect has excellent antithrombotic activity and biocompatibility (the suppression and prevention effects of the adhesion and attachment of the platelets and the suppression and prevention effects of the activation of the platelets) and, for example, has excellent suppression and prevention effects of the adhesion and attachment of the platelets.

EXAMPLES

Exemplary effects of the present invention will be explained using the following examples and a comparative example. But the technical scope of the present invention is not limited to the following examples. In the following examples, experiments were carried out at room temperature (25° C.) unless otherwise specified. In addition, unless otherwise specified, "%" and "part" mean "% by weight" and "parts by weight", respectively.

Preparation Example 1: Synthesis of PMEA Having Weight Average Molecular Weight of 310,000

60 g (0.46 mol) of 2-methoxyethyl acrylate (MEA) was dissolved in 135 g of methanol and put in a 4-neck flask, $N_2$ bubbling was carried out at 50° C. for 1 hour, and thereby a monomer solution (1) was prepared. Additionally, 0.06 g of 2,2'-azobis(4-methoxy-2,4-dimethylvaleronitrile) (V-70, manufactured by Wako Pure Chemical Industries, Ltd.) was dissolved in 5 g of methanol, and a polymerization initiator solution (1) was prepared. Next, the polymerization initiator solution (1) was added to the monomer solution (1), and the polymerization reaction was carried out at 50° C. for 5 hours. After polymerization for a predetermined time, the polymerization solution was added dropwise to ethanol, and the precipitated polymer (PMEA (1)) was recovered. The weight average molecular weight of the recovered polymer (PMEA (1)) was measured and was 310,000.

Preparation Example 2: Synthesis of PMEA Having Weight Average Molecular Weight of 420,000

80 g (0.61 mol) of 2-methoxyethyl acrylate (MEA) was dissolved in 115 g of methanol and put in a 4-neck flask, $N_2$ bubbling was carried out at 50° C. for 1 hour, and thereby a monomer solution (2) was prepared. Additionally, 0.08 g of 2,2'-azobis(4-methoxy-2,4-dimethylvaleronitrile) (V-70, manufactured by Wako Pure Chemical Industries, Ltd.) was dissolved in 5 g of methanol, and a polymerization initiator solution (2) was prepared. Next, the polymerization initiator solution (2) was added to the monomer solution (2), and the polymerization reaction was carried out at 50° C. for 5 hours. After polymerization for a predetermined time, the polymerization solution was added dropwise to ethanol, and the precipitated polymer (PMEA (2)) was recovered. The weight average molecular weight of the recovered polymer (PMEA (2)) was measured and was 420,000.

Preparation Example 3: Synthesis of PMEA Having Weight Average Molecular Weight of 490,000

80 g (0.61 mol) of 2-methoxyethyl acrylate (MEA) was dissolved in 115 g of methanol and put in a 4-neck flask, $N_2$ bubbling was carried out at 43° C. for 1 hour, and thereby a monomer solution (3) was prepared. Additionally, 0.08 g of 2,2'-azobis(4-methoxy-2,4-dimethylvaleronitrile) (V-70, manufactured by Wako Pure Chemical Industries, Ltd.) was dissolved in 5 g of methanol, and a polymerization initiator solution (3) was prepared. Next, the polymerization initiator solution (3) was added to the monomer solution (3), and the polymerization reaction was carried out at 43° C. for 8 hours. After polymerization for a predetermined time, the polymerization solution was added dropwise to ethanol, and the precipitated polymer (PMEA (3)) was recovered. The weight average molecular weight of the recovered polymer (PMEA (3)) was measured and was 490,000.

Preparation Example 4: Synthesis of PMEA Having Weight Average Molecular Weight of 85,000

20 g (0.16 mol) of 2-methoxyethyl acrylate (MEA) was dissolved in 75 g of toluene and put in a 4-neck flask, $N_2$ bubbling was carried out at 80° C. for 1 hour, and thereby a monomer solution (4) was prepared. Additionally, 0.02 g of 2,2-azobisisobutyronitrile (AIBN, manufactured by Wako Pure Chemical Industries, Ltd.) was dissolved in 5 g of toluene, and a polymerization initiator solution (4) was prepared. Next, the polymerization initiator solution (4) was added to the monomer solution (4), and the polymerization reaction was carried out at 80° C. for 8 hours. After polymerization for a predetermined time, the polymerization solution was added dropwise to normal hexane, and the precipitated polymer (PMEA (4)) was recovered. The weight average molecular weight of the recovered polymer (PMEA (4)) was measured and was 85,000.

Preparation Example 5: Synthesis of PMEA Having Weight Average Molecular Weight of 410,000

15 g (0.115 mol) of methoxyethyl acrylate (MEA) was dissolved in 25 g of methanol and put in a 4-neck flask, $N_2$ bubbling was carried out at 50° C. for 1 hour, and thereby a monomer solution (5) was prepared. Additionally, 0.015 g of 2,2'-azobis(4-methoxy-2,4-dimethylvaleronitrile) (V-70, manufactured by Wako Pure Chemical Industries, Ltd.) was dissolved in 3 g of methanol, and a polymerization initiator solution (5) was prepared. Next, the polymerization initiator solution (5) was added to the monomer solution (5), and the polymerization reaction was carried out at 50° C. for 5 hours in a nitrogen gas atmosphere. After polymerization for a predetermined time, the polymerization solution was added dropwise to ethanol, and the precipitated polymer (PMEA (5)) was recovered. The weight average molecular weight of the recovered polymer (PMEA (5)) was measured and was 410,000.

Example 1

PMEA (1) (weight average molecular weight=310,000) synthesized in Preparation Example 1 above was dispersed in a mixed solvent of water and methanol (mixing ratio of water:methanol=95:5 (volume ratio)) so that the concentration of PMEA (1) becomes 0.1% by weight, and therefore a coating solution (1) having a surface tension of 46 dyn/cm was prepared.

Additionally, approximately 50,000 porous hollow fiber membranes for gas exchange made of porous polypropylene having the inner diameter of 120 μm, the outer diameter of 170 μm, the wall thickness of 25 μm and the porosity of approximately 40% by volume were accommodated in a housing, and therefore a hollow fiber membrane artificial lung (a) of an outside blood flow type that has a membrane area of 1.9 m$^2$ and that is described in FIG. 1 of JP-A-11-114056 was produced.

The blood flow path of this artificial lung (a) was filled with the coating solution (1) prepared above and allowed to stand at 25° C. for 120 seconds, and then the coating solution was removed, air of a flow volume of 80 L was allowed to flow, the hollow fiber membranes were dried, and therefore a hollow fiber membrane artificial lung (1) of an outside blood flow type having hollow fiber membranes in which a coat is formed on the outer surfaces was prepared. The hollow fiber membrane artificial lung (1) of an outside blood flow type obtained as above may be referred to as the artificial lung (1).

Example 2

PMEA (1) (weight average molecular weight=310,000) synthesized in Preparation Example 1 above was dispersed in a mixed solvent of water and methanol (mixing ratio of water:methanol=85:15 (volume ratio)) so that the concentration of PMEA (1) becomes 0.1% by weight, and therefore a coating solution (2) having a surface tension of 42 dyn/cm was prepared.

A hollow fiber membrane artificial lung of an outside blood flow type (2) was prepared in the same manner as Example 1 except that the coating solution (2) was used instead of the coating solution (1) in Example 1. The hollow fiber membrane artificial lung (2) of an outside blood flow type obtained as above may be referred to as the artificial lung (2).

Example 3

PMEA (2) (weight average molecular weight=420,000) synthesized in Preparation Example 2 above was dispersed in a mixed solvent of water and methanol (mixing ratio of water:methanol=95:5 (volume ratio)) so that the concentration of PMEA (2) becomes 0.1% by weight, and therefore a coating solution (3) having a surface tension of 46 dyn/cm was prepared.

A hollow fiber membrane artificial lung of an outside blood flow type (3) was prepared in the same manner as Example 1 except that the coating solution (3) was used instead of the coating solution (1) in Example 1. The hollow fiber membrane artificial lung (3) of an outside blood flow type obtained as above may be referred to as the artificial lung (3).

Example 4

PMEA (3) (weight average molecular weight=490,000) synthesized in Preparation Example 3 above was dispersed in a mixed solvent of water and methanol (mixing ratio of water:methanol=95:5 (volume ratio)) so that the concentration of PMEA (3) becomes 0.1% by weight, and therefore a coating solution (4) having a surface tension of 46 dyn/cm was prepared.

A hollow fiber membrane artificial lung of an outside blood flow type (4) was prepared in the same manner as Example 1 except that the coating solution (4) was used instead of the coating solution (1) in Example 1. The hollow fiber membrane artificial lung (4) of an outside blood flow type obtained as above may be referred to as the artificial lung (4).

Example 5

PMEA (4) (weight average molecular weight=85,000) synthesized in Preparation Example 4 above was dispersed in a mixed solvent of water and methanol (mixing ratio of water:methanol=95:5 (volume ratio)) so that the concentration of PMEA (4) becomes 0.1% by weight, and therefore a coating solution (5) having a surface tension of 46 dyn/cm was prepared.

A hollow fiber membrane artificial lung of an outside blood flow type (5) was prepared in the same manner as Example 1 except that the coating solution (5) was used instead of the coating solution (1) in Example 1. The hollow fiber membrane artificial lung (5) of an outside blood flow type obtained as above may be referred to as the artificial lung (5).

Comparative Example 1

PMEA (weight average molecular weight=310,000) synthesized in Preparation Example 1 above was dispersed in a mixed solvent of water, methanol, and ethanol (mixing ratio of water:methanol:ethanol=6:1:3 (volume ratio)) so that the concentration of PMEA becomes 0.1% by weight, and therefore a coating solution (6) having a surface tension of 37 dyn/cm was prepared.

A hollow fiber membrane artificial lung of an outside blood flow type (6) was prepared in the same manner as Example 1 except that the coating solution (6) was used instead of the coating solution (1) in Example 1. The hollow fiber membrane artificial lung (6) of an outside blood flow type obtained as above may be referred to as the artificial lung (6).

Reference Example 1

PMEA (1) (weight average molecular weight=310,000) synthesized in Preparation Example 1 above was dispersed in a mixed solvent of water, methanol, and ethanol (mixing ratio of water:methanol:ethanol=6:1:3 (volume ratio)) so that the concentration of PMEA (1) becomes 0.1% by weight, and therefore a coating solution (7) having a surface tension of 37 dyn/cm was prepared.

Additionally, approximately 20,000 porous hollow fiber membranes for gas exchange made of porous polypropylene having the inner diameter of 195 μm, the outer diameter of 295 μm, the wall thickness of 50 μm and the porosity of approximately 35% were accommodated in a housing, and therefore a hollow fiber membrane artificial lung (b) of an outside blood flow type that has a membrane area of 1.8 m$^2$ and that is described in FIG. 1 of JP-A-11-114056 (corresponding to EP 0 908 191 A1 or U.S. Pat. No. 6,495,101 B1) was produced.

The blood flow path of this artificial lung (b) was filled with the coating solution (7) prepared above and allowed to stand at 25° C. for 120 seconds, and then the coating solution was removed, air of a flow volume of 80 L was allowed to flow, the hollow fiber membranes were dried, and therefore a hollow fiber membrane artificial lung (7) of an outside blood flow type was prepared. The hollow fiber membrane artificial lung (7) of an outside blood flow type obtained as above may be referred to as the artificial lung (7).

Experiment 1: Test on Blood Plasma Leakage Resistance Performance

With respect to the artificial lungs (1), (2), and (5) of Examples 1, 2 and 5, and the artificial lung (6) of Comparative Example 1, and the artificial lung (7) of Reference Example 1, the blood plasma leakage resistance performance was evaluated by using the following method. The results are shown in the following Table 1.

Figure 8:
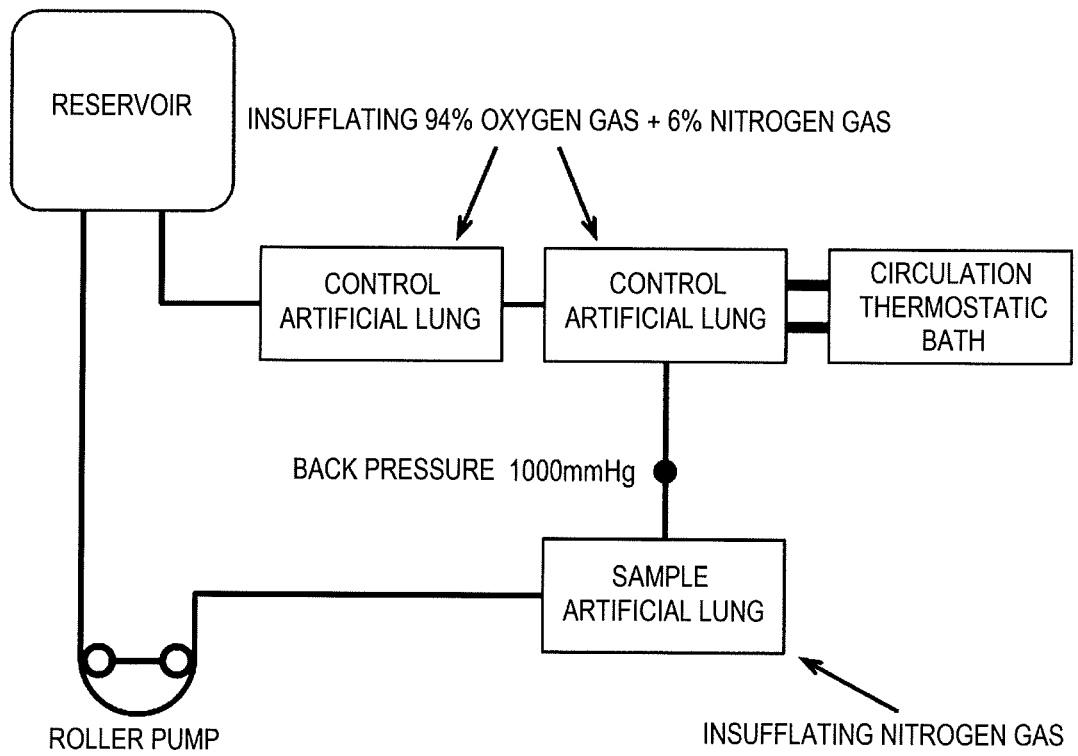
FIG. 8 is a view showing a test system of blood plasma leakage resistance performance test in Experiment 1, according to one aspect.

FIG. 8 is a view showing a test system of the blood plasma leakage resistance performance test. As shown in FIG. 8, this test system is composed of a reservoir, a roller pump, and the artificial lung with a built-in heat exchanger (also referred to as "a control artificial lung") which is not an evaluation sample. Among these, as the reservoir, a soft bag type is used. Every circuit of this test is a closed circuit that is not open to the atmosphere.

Bovine blood plasma is used as a working fluid, and the blood plasma concentrated (water removed) with a hemo-concentrator such that a surface tension becomes 43±2 dyn/cm in order to accelerate blood plasma leakage is used as a working fluid. This bovine blood plasma (working fluid) is circulated in the circuit by the roller pump and the temperature is controlled to 37±0.5° C. by a heat exchanger. Oxygen gas (94% by volume oxygen gas and 6% by volume nitrogen gas) is insufflated into the control artificial lung to raise the oxygen partial pressure in the bovine blood plasma, and the bovine blood plasma with a high oxygen partial pressure of approximately 650±50 mmHg of oxygen partial pressure is allowed to flow into the artificial lung (hereinafter also referred to as the "sample artificial lung") which is an evaluation sample. By insufflating nitrogen gas (100% by volume nitrogen gas) into the sample artificial lung, the oxygen partial pressure of the blood plasma at the outlet of the sample artificial lung decreases as compared with that at the inlet of the sample artificial lung. The gas exchange performance can be continuously measured by a difference in this oxygen partial pressure.

The experiment was conducted for 9 hours, and the difference in the oxygen partial pressure between the start of the experiment (0 hour) and the 9th hour after the start of the experiment is evaluated as the blood plasma leakage resistance performance. The smaller the oxygen partial pressure difference becomes, the higher the blood plasma leakage resistance performance becomes. In addition, in order to accelerate the blood plasma leakage, a back pressure (outlet pressure) of the sample artificial lung is set to 1,000 mmHg.

TABLE 1

| | | Thickness of membrane for gas exchange (μm) | Surface tension of coating solution (dyn/cm) | Blood plasma leakage resistance performance (mmHg) |
|---|---|---|---|---|
| Example 1 | Artificial lung (1) | 25 | 46 | 6.8 |
| Example 2 | Artificial lung (2) | 25 | 42 | 8.7 |
| Example 5 | Artificial lung (5) | 25 | 46 | 7.0 |
| Comparative Example 1 | Artificial lung (6) | 25 | 37 | 19.5 |
| Reference Example 1 | Artificial lung (7) | 50 | 37 | 6.4 |

From the results in Table 1 above, it was found that the artificial lungs (1), (2) and (5) according to exemplary aspects can significantly suppress the blood plasma leakage (that is, the blood plasma leakage resistance performance is significantly low) compared to the artificial lung (6) of Comparative Example 1 in which the hollow fiber membranes are coated with a coating solution having the surface tension outside of the range of 40 to 55 dyn/cm.

In addition, from the results of Table 1 above, it was found that the artificial lung according to one aspect can effectively suppress the blood plasma leakage after circulation to the same extent as that of Reference Example 1 having a thick wall thickness even in the hollow fiber membranes having a thin wall thickness. In the artificial lung (7) of Reference Example 1, the blood plasma leakage resistance performance is low (blood plasma leakage can be suppressed). Without wishing to be bound to any theory, it is considered that the reason for this is because the hollow fiber membranes have a thick wall thickness, even if the blood plasma penetrates into the holes of the hollow fiber membranes, the plasma does not pass through the lumen of the hollow fiber, which makes the blood plasma leakage resistance performance low (blood plasma leakage can be suppressed).

Example 6

PMEA (1) (weight average molecular weight=310,000) synthesized in Preparation Example 1 above was dispersed in a mixed solvent of water and methanol (mixing ratio of water:methanol=95:5 (volume ratio)) so that the concentration of PMEA (1) becomes 0.2% by weight, and therefore a coating solution (8) having a surface tension of 46 dyn/cm was prepared.

Example 7

PMEA (2) (weight average molecular weight=420,000) synthesized in Preparation Example 2 above was dispersed in a mixed solvent of water and methanol (mixing ratio of water:methanol=95:5 (volume ratio)) so that the concentration of PMEA (2) becomes 0.2% by weight, and therefore a coating solution (9) having a surface tension of 46 dyn/cm was prepared.

Example 8

PMEA (3) (weight average molecular weight=490,000) synthesized in Preparation Example 3 above was dispersed in a mixed solvent of water and methanol (mixing ratio of water:methanol=95:5 (volume ratio)) so that the concentration of PMEA (3) becomes 0.2% by weight, and therefore a coating solution (10) having a surface tension of 46 dyn/cm was prepared.

Example 9

PMEA (4) (weight average molecular weight=85,000) synthesized in Preparation Example 4 above was dispersed in a mixed solvent of water and methanol (mixing ratio of water:methanol=95:5 (volume ratio)) so that the concentration of PMEA (4) becomes 0.2% by weight, and therefore a coating solution (11) having a surface tension of 46 dyn/cm was prepared.

Experiment 2: Test on Elution Amount

With respect to the coating solutions (8) to (11) prepared in Examples 6 to 9 above, the elution amount of the PMEA coat was evaluated using the reduction rate of the PMEA application amount as an index by the following method. The results are shown in the following Table 2.

A biaxially oriented polypropylene film (weight a before application (g)) having a thickness of 50 μm and a size of 7.5 cm×7.5 cm which are measured in advance, was prepared. Each coating solution was applied to this polypropylene film. After application, the coating film was dried at room temperature (25° C.) for 72 hours, and therefore the PMEA coat was formed on the polypropylene film. The weight (weight b after drying the application (g)) of the film on which the PMEA coat obtained as above is formed was measured. Next, the film on which the PMEA coat is formed was immersed in a saline solution, and was put in an incubator set at 37° C. for 5 days. After the immersion for a predetermined time, the film was taken out from the saline solution, washed with distilled water and dried at 50° C. for 48 hours. Then, the weight of the film after drying (the weight c after immersion (g)) was measured.

The application amount of PMEA before the immersion in the saline solution [=(weight b after drying the application (g))−(weight a before application (g))], and the application amount of PMEA after the immersion in the saline solution [=(weight c after immersion (g))−(weight a before application (g))] were calculated, and from these values, the reduction rate (%) of the application amount of PMEA was calculated based on Formula (1).

$$\text{Reduction rate (\%) of application amount of } PMEA = \frac{(\text{weight } c \text{ after immersion }(g)) - (\text{weight } a \text{ before application }(g))}{(\text{weight } b \text{ after drying the application }(g)) - (\text{weight } a \text{ before application }(g))} \times 100$$

solution can be effectively suppressed by adjusting the surface tension of the coating solution and further increasing the weight average molecular weight of the polymer. In addition, from the results, it is expected that the elution amount of the polymer into blood can be effectively reduced by adjusting the surface tension of the coating solution and further increasing the weight average molecular weight of the polymer.

Example 10

PMEA (5) (weight average molecular weight=410,000) synthesized in Preparation Example 5 above was dispersed in a mixed solvent of water and methanol (mixing ratio of water:methanol=95:5 (volume ratio)) so that the concentration of PMEA (5) becomes 0.05% by weight, and therefore a coating solution (12) having a surface tension of 48 dyn/cm was prepared.

A hollow fiber membrane artificial lung (a) of an outside blood flow type was prepared in the same manner as Example 1 above.

The blood flow path of this artificial lung (a) was filled with the coating solution (12) prepared above and allowed to stand at 25° C. for 120 seconds, and then the coating solution was removed, followed by air drying at room temperature (25° C.) for 240 minutes, the hollow fiber membranes were dried, and therefore a hollow fiber membrane artificial lung (8) of an outside blood flow type having hollow fiber membranes in which a coat is formed on the outer surface was prepared. The hollow fiber membrane artificial lung (8) of an outside blood flow type obtained as above may be referred to as the artificial lung (8).

Experiment 3: Blood Circulation Test

The antithrombotic activity of the artificial lung (8) obtained in Example 10 above was evaluated by the following method. That is, the artificial lung (8) is incorporated

TABLE 2

|  |  | Weight average molecular weight of PMEA | Surface tension of coating solution (dyn/cm) | Weight before application (a) | Weight after drying application (b) | (b)-(a) | Weight after immersion (c) | (c)-(a) | Reduction rate (%) of PMEA application amount |
|---|---|---|---|---|---|---|---|---|---|
| Example 6 | Coating solution (8) | 310,000 | 46 | 0.2510 g | 0.2592 g | 0.0082 g | 0.2589 g | 0.0079 g | 3.7% |
| Example 7 | Coating solution (9) | 420,000 | 46 | 0.2508 g | 0.2595 g | 0.0087 g | 0.2592 g | 0.0084 g | 3.4% |
| Example 8 | Coating solution (10) | 490,000 | 46 | 0.2511 g | 0.2599 g | 0.0088 g | 0.2597 g | 0.0086 g | 2.3% |
| Example 9 | Coating solution (11) | 85,000 | 46 | 0.2509 g | 0.2589 g | 0.0080 g | 0.2570 g | 0.0061 g | 23.8% |

The results in Table 2 show that in the coat formed by the coating solutions (8) to (10) of Examples 6 to 8, the reduction rate of the application amount of PMEA was significantly lower compared to the coat formed by the coating solution (11) of Example 9. From these results, it is considered that a coated layer becomes more stable when using the coat by PMEAs (1) to (3) of Examples 6 to 8 than the coat by PMEA (4) having a lower molecular weight of Example 9.

In addition, by considering all the results of Table 1, it is presumed that the elution of the polymer into the saline into an extracorporeal circulation circuit (blood circulation circuit), and the artificial lung was filled with diluted fresh human blood (heparin: 0.2 unit/ml) mixed with 90 ml of fresh human blood to which heparin (0.45 unit/ml) was added, and 110 ml of a saline solution. The diluted fresh human blood was circulated in the artificial lung (8) at room temperature (25° C.) at a rate of 500 ml/min. Sixty minutes after the start of the circulation, the blood was sampled from the extracorporeal circulation circuit, the number of platelets was measured, and the ratio of the number of platelets after circulation (platelet number maintenance rate) to the number of platelets before the start of circulation (100%) was obtained. As a result, the platelet number maintenance rate was 91%.

From the results, it is found that the artificial lung according to an exemplary aspect can maintain the platelets at a high maintenance rate. That is, it can be confirmed that there is less decrease in the number of platelets caused by aggregation of platelets starting from activation of a coagulation system and a platelet system, attachment to a base material, and the like, and that excellent antithrombotic activity is exhibited.

The detailed description above describes exemplary embodiments of an artificial lung and exemplary embodiments of a method for manufacturing an artificial lung. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A method for manufacturing an artificial lung comprising a plurality of porous hollow fiber membranes for gas exchange comprising a hydrophobic polymer material, wherein the hollow fiber membranes have inner surfaces forming lumens and outer surfaces, the method comprising:
coating the inner surfaces forming the lumens of the hollow fiber membranes or the outer surfaces with a polymer-containing solution that has a surface tension of 40 to 55 dyn/cm and that contains a solvent and a polymer having a structural unit represented by Formula (I):

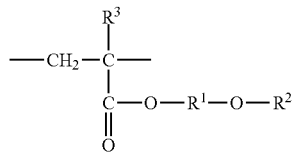

(I)

wherein in Formula (I), $R^3$ represents a hydrogen atom or a methyl group, $R^1$ represents an alkylene group having 1 to 4 carbon atoms, and $R^2$ represents an alkyl group having 1 to 4 carbon atoms.

2. The manufacturing method according to claim 1, wherein the hollow fiber membranes are for accommodating a flow of an oxygen-containing gas inside the lumens, and the outer surfaces of the hollow fiber membranes are for contacting blood, and
the outer surfaces are coated with the polymer-containing solution.

3. The manufacturing method according to claim 1, wherein the hollow fiber membranes are for accommodating blood inside the lumens, and the outer surfaces of the hollow fiber membranes are for contacting a flow of an oxygen-containing gas, and
the inner surfaces are coated with the polymer-containing solution.

4. The manufacturing method according to claim 1, wherein the polymer has a weight average molecular weight of 250,000 to 600,000.

5. The manufacturing method according to claim 1, wherein a wall thickness between the inner surfaces and the outer surfaces is 20 µm or more and less than 50 µm.

6. The manufacturing method according to claim 1, wherein the solvent contains water and methanol in a mixing ratio of 5:1 to 99:1, based on the volume of the water and methanol.

7. The manufacturing method according to claim 1, wherein the outer surfaces of the hollow fiber membranes are coated with the polymer-containing solution, and wherein the polymer-containing solution penetrates into a part of the outer surfaces.

8. An artificial lung, comprising:
a plurality of porous hollow fiber membranes for gas exchange comprising a hydrophobic polymer material, wherein the hollow fiber membranes have inner surfaces forming lumens and outer surfaces, and
wherein at least one of the inner surfaces or the outer surfaces is coated with a polymer-containing solution that has a surface tension of 40 to 55 dyn/cm and that contains a solvent and a polymer having a structural unit represented by Formula (I):

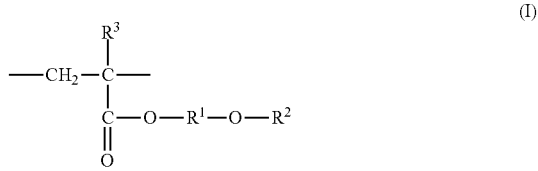

(I)

wherein in Formula (I), $R^3$ represents a hydrogen atom or a methyl group, $R^1$ represents an alkylene group having 1 to 4 carbon atoms, and $R^2$ represents an alkyl group having 1 to 4 carbon atoms.

9. The artificial lung according to claim 8, wherein the hollow fiber membranes are for accommodating a flow of an oxygen-containing gas inside the lumens, and the outer surfaces of the hollow fiber membranes are for contacting blood, and
the outer surfaces are coated with the polymer-containing solution.

10. The artificial lung according to claim 8, wherein the hollow fiber membranes are for accommodating blood inside the lumens, and the outer surfaces of the hollow fiber membranes are for contacting a flow of an oxygen-containing gas, and
the inner surfaces are coated with the polymer-containing solution.

11. The artificial lung according to claim 8, wherein the polymer has a weight average molecular weight of 250,000 to 600,000.

12. The artificial lung according to claim 8, wherein a wall thickness between the inner surfaces and the outer surfaces is 20 µm or more and less than 50 µm.

13. The artificial lung according to claim 12, wherein the wall thickness between the inner surfaces and the outer surfaces is in a range of from 25 to 30 µm.

14. The artificial lung according to claim 8, wherein the solvent contains water and methanol in a mixing ratio of 5:1 to 99:1, based on the volume of the water and methanol.

15. The artificial lung according to claim 8, wherein a blood plasma leakage resistance performance of the artificial lung is 15 mmHg or less.

16. The artificial lung according to claim 8, wherein the outer surfaces of the hollow fiber membranes are coated with the polymer-containing solution, and wherein the polymer-containing solution penetrates into a part of the outer surfaces.

17. An artificial lung, comprising:
a plurality of porous hollow fiber membranes for gas exchange comprising a hydrophobic polymer material, wherein the hollow fiber membranes have inner surfaces forming lumens and outer surfaces,
wherein a wall thickness between the inner surfaces and the outer surfaces is 20 μm or more and less than 50 μm,
wherein at least one of the inner surfaces or the outer surfaces is coated with a coating that contains a polymer having a structural unit represented by Formula (I):

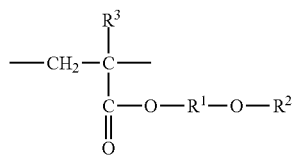

(I)

wherein in Formula (I), $R^3$ represents a hydrogen atom or a methyl group, $R^1$ represents an alkylene group having 1 to 4 carbon atoms, and $R^2$ represents an alkyl group having 1 to 4 carbon atoms, and wherein a blood plasma leakage resistance performance of the artificial lung is 15 mmHg or less.

18. The artificial lung according to claim 17,
wherein the hollow fiber membranes are for accommodating a flow of an oxygen-containing gas inside the lumens, and the outer surfaces of the hollow fiber membranes are for contacting blood, and
the outer surfaces are coated with the coating containing the polymer having a structural unit represented by Formula (I).

19. The artificial lung according to claim 17,
wherein the hollow fiber membranes are for accommodating blood inside the lumens, and the outer surfaces of the hollow fiber membranes are for contacting a flow of an oxygen-containing gas, and
the inner surfaces are coated with the coating containing the polymer having a structural unit represented by Formula (I).

20. The artificial lung according to claim 17,
wherein the polymer has a weight average molecular weight of 250,000 to 600,000.

21. The artificial lung according to claim 17, wherein the outer surfaces are coated with the coating containing the polymer having a structural unit represented by Formula (I), and wherein the coating penetrates into a part of the outer surfaces.

* * * * *